(12) United States Patent
Miller et al.

(10) Patent No.: US 6,566,345 B2
(45) Date of Patent: May 20, 2003

(54) POLYACID/POLYALKYLENE OXIDE FOAMS AND GELS AND METHODS FOR THEIR DELIVERY

(75) Inventors: Mark E. Miller, Pismo Beach, CA (US); Stephanie M. Cortese, Atascadero, CA (US); Herbert E. Schwartz, Redwood City, CA (US); William G. Oppelt, Arroyo Grande, CA (US)

(73) Assignee: FzioMed, Inc., San Luis Obispo, CA (US)

( * ) Notice: Subject to any disclaimer, the term of this patent is extended or adjusted under 35 U.S.C. 154(b) by 20 days.

(21) Appl. No.: 09/843,194

(22) Filed: Apr. 26, 2001

(65) Prior Publication Data

US 2002/0028181 A1 Mar. 7, 2002

Related U.S. Application Data

(60) Provisional application No. 60/200,637, filed on Apr. 28, 2000.

(51) Int. Cl.⁷ .................. A61K 31/717; A61K 31/715; A61K 31/77; A61K 31/737; A61K 31/728; A61K 31/722; A61K 31/734

(52) U.S. Cl. ................... 514/54; 514/55; 514/57; 514/58; 424/78.18; 424/78.3

(58) Field of Search .................. 514/54, 55, 58, 514/57; 424/78.18, 78.3

(56) References Cited

U.S. PATENT DOCUMENTS

| | | | |
|---|---|---|---|
| 3,064,313 A | 11/1962 | Butler | 18/57 |
| 3,328,259 A | 6/1967 | Anderson | 167/84 |
| 3,387,061 A | 6/1968 | Smith et al. | 260/874 |
| 4,024,073 A | 5/1977 | Shimizu et al. | 252/316 |
| 4,141,973 A | 2/1979 | Balazs | 424/180 |
| 4,181,718 A | 1/1980 | Mason et al. | 424/180 |
| 4,442,258 A | 4/1984 | Sunakawa et al. | 524/767 |
| 4,610,863 A | 9/1986 | Tewari et al. | 423/338 |
| 4,616,644 A | 10/1986 | Saferstein et al. | 128/156 |
| 4,684,558 A | 8/1987 | Keusch et al. | 428/40 |
| 4,713,243 A | 12/1987 | Schiraldi et al. | 424/676 |
| 4,768,523 A | 9/1988 | Cahalan et al. | 128/785 |
| 4,772,419 A | 9/1988 | Malson et al. | 252/315.1 |
| 4,853,374 A | 8/1989 | Allen | 514/57 |
| 4,937,254 A | 6/1990 | Sheffield et al. | 514/420 |
| 4,937,270 A | 6/1990 | Hamilton et al. | 514/777 |
| 4,983,585 A | 1/1991 | Pennell et al. | 514/57 |
| 5,017,229 A | 5/1991 | Burns et al. | 106/162 |
| 5,066,709 A | 11/1991 | Chaudhuri et al. | 524/516 |
| 5,068,225 A | 11/1991 | Pennell et al. | 514/57 |
| 5,080,821 A | 1/1992 | Lutringer | 252/170 |
| 5,080,893 A | 1/1992 | Goldberg et al. | 514/57 |
| 5,093,319 A | 3/1992 | Higham et al. | 514/55 |
| 5,126,086 A | 6/1992 | Stoffel | 264/130 |
| 5,140,016 A | 8/1992 | Goldberg et al. | 514/57 |
| 5,156,839 A | 10/1992 | Pennell et al. | 424/78.37 |
| 5,169,037 A | 12/1992 | Davies et al. | 222/402.1 |
| 5,266,326 A | 11/1993 | Barry et al. | 424/423 |
| 5,298,488 A | 3/1994 | Kojima et al. | 514/8 |
| 5,354,790 A | 10/1994 | Keusch et al. | 523/300 |
| 5,356,883 A | 10/1994 | Kuo et al. | 514/54 |
| 5,462,749 A | 10/1995 | Rencher | 424/484 |
| 5,502,081 A | 3/1996 | Kuo et al. | 514/777 |
| 5,512,329 A | 4/1996 | Guire et al. | 427/508 |
| 5,532,221 A | 7/1996 | Huang et al. | 514/53 |
| 5,621,093 A | 4/1997 | Swann et al. | 536/55.2 |
| 5,681,873 A | 10/1997 | Norton et al. | 523/115 |
| 5,711,958 A | 1/1998 | Cohn et al. | 424/423 |
| 5,800,832 A | 9/1998 | Tapolsky et al. | 424/449 |

(List continued on next page.)

FOREIGN PATENT DOCUMENTS

| | | |
|---|---|---|
| EP | 0 138 572 A2 | 4/1985 |
| EP | 0 193 510 A1 | 9/1986 |
| EP | 0 265 561 A1 | 10/1986 |
| EP | 0 264 719 A2 | 4/1988 |
| EP | 0 581 581 A2 | 2/1994 |
| JP | 40-9241973 A | 9/1997 |
| WO | WO 84/03302 | 8/1984 |
| WO | WO 86/00912 | 2/1986 |
| WO | WO 89/02445 | 3/1989 |
| WO | WO 90/10020 | 9/1990 |

OTHER PUBLICATIONS

Elkins, et al., *Adhesion prevention by solutions of sodium carboxymethylcellulose in the rat. I.* Fertility and Sterility, vol. 41, No. 6, 926–928, Jun. 1984.

(List continued on next page.)

*Primary Examiner*—Alton N. Pryor
(74) *Attorney, Agent, or Firm*—Fliesler, Dubb, Meyer & Lovejoy LLP

(57) ABSTRACT

The present invention relates to improved methods for delivering bioadhesive, bioresorbable, anti-adhesion compositions. Antiadhesion compositions can be made of intermacromolecular complexes of carboxyl-containing polysaccharides, polyethers, polyacids, polyalkylene oxides, multivalent cations and/or polycations. The polymers are associated with each other, and are then used as fluids, gels or foams. By providing a product bag, the compositions can be delivered as gels or as sprays. By dissolving propellant gases in the compositions, the materials can be delivered as foams, which have decreased density, and therefore can adhere to surfaces that previously have been difficult to coat with antiadhesion gels. Delivery systems can also provide mechanisms for expelling more product, and for directing the flow of materials leaving the delivery system. Bioresorbable, bioadhesive, anti-adhesion, and/or hemostatic compositions are useful in surgery to prevent the formation and reformation of post-surgical adhesions. The biological and physical properties of such compositions can be varied as needed by carefully adjusting the pH and/or cation content of the polymer casting solutions, polyacid composition, the polyalkylene oxide composition, or by selecting the solids content of the composition. Antiadhesion compositions may also be used to lubricate tissues and/or medical instruments, and/or deliver drugs to the surgical site and release them locally.

16 Claims, 11 Drawing Sheets

U.S. PATENT DOCUMENTS

| | | | |
|---|---|---|---|
| 5,858,746 A | 1/1999 | Hubbell et al. | 435/177 |
| 5,874,417 A | 2/1999 | Prestwich et al. | 514/54 |
| 5,906,997 A | 5/1999 | Schwartz et al. | 514/781 |
| 5,944,754 A | 8/1999 | Vacanti | 623/11 |
| 5,955,096 A | 9/1999 | Santos et al. | 424/434 |
| 5,968,500 A | 10/1999 | Robinson | 424/78.08 |
| 5,968,542 A | 10/1999 | Tipton | 424/423 |
| 5,985,312 A | 11/1999 | Jacob et al. | 424/434 |
| 5,989,215 A | 11/1999 | Delmotte et al. | 604/82 |
| 6,017,301 A | 1/2000 | Schwartz et al. | 547/781 |
| 6,054,122 A | 4/2000 | MacPhee et al. | 424/94.4 |
| 6,096,309 A | 8/2000 | Prior et al. | 424/94.63 |

OTHER PUBLICATIONS

Elkins, et al., *Adhesion prevention by solutions of sodium carboxymethylcellulose in the rat. I.* Fertility and Sterility, vol. 41, No. 6, 929–932, Jun. 1984.

Wiseman, *Polymer for the Prevention of Surgical Adhesions*, Johnson & Johnson Medical, Inc., Arlington, Texas, 369–421.

Merrill, *Poly(Ethylene Oxide) and Blood Contact, A Chronicle of One Laboratory*, 199–229.

Chalkol, *Platelet Interaction with Poly(ethylene Oxide) Networks*, AIChE Journal, vol. 36, No. 7, 994–1002, Jul. 1990.

Bottenberg, et al., *Development and Testing of Bloodhesive, Fluoride–containing Slow–release Tablets for Oral Use*, J. Pharm. Pharmacol., 43:457–464, 1991.

Amiji, *Permeability and blood compatibility of chitosan-poly(ethylene oxide) blend membranes for haemodialysis*, Biomaterials, 16, 593–599, 1995.

Dieckman, et al., *Carboxymethylcellulose in the Free Acid Form*, Industrial and Engineering Chemistry, vol. 45, No. 10, 2287–2290.

Gurny, et al., *Bioadhesive intraoral release systems: design, testing and analysis*, Biomaterials, vol. 5, 336–340, 1984.

Chen, et al., *Composition Producing Adhesion Through Hydration*, 163–181.

Kulicke, et al., *Characterization of aqueous carboxymethylcellulose solutions in terms of their molecular structure and its influence on rheological behavior*, Polymer, vol. 37, No. 13, 2723–2731, 1996.

Ohno, et al., *Interpolymer Complex Formation of Polysaccharides with Poly(ethylene oxide) or Poly(1–vinyl–2–pyrrolidine) through Hydrogen Bond*, Makromol. Chem. Rapid Comun., 2, 511–515, 1981.

*Acqualon, Sodium Carboxymethylcellulose, Physical and Chemical Properties*, Hercules, Inc., 1–27.

Didishelm, et al., *Hemarologic and Coagulation Studies in Various Animal Species*, J. Lab. & Clin. Med., 866–875, Jun. 1959.

Harris, et al., *Analysis of the Kinetics of peritoneal adhesion formation in the rat and evaluation of potential antiadhesive agents*, Surgery, 663–669, Jun. 1995.

Becker, et al., *Prevention of Postoperative Abdominal Adhesions by a Sodium Hyaluronate–based Bioresorbable Membrane: A Prospective, Randomized, Double–Blind Multicenter Study*, Journal of American College of Surgeons, vol. 183, 297–306, Oct. 1996.

Interceed (TC7) Adhesion Barrier Study Group, *Prevention of postsurgical adhesions by INTERCEED (TC7), *an absorbable adhesion barrier: a prospective, randomized multicenter clinical study*, Fertility and Sterility, vol. 51, No. 6, 933–938, Jun. 1989.

Diamond, et al., *Reduction of adhesions after uterine myomectomy by Seprafilm* membrane (HAL–F): a blinded, prospective, randomized, multicenter clinical study*, Fertility and Sterility, vol. 66, No. 6, 904–910, Dec. 1996.

Sung, et al., *Swelling properties of hyaluronic acid ester membranes*, Journal of Membrane Science, 92, 157–167, 1994.

Braun, *Poly (Ethylene Oxide)*, Union Carbide Corporation, Union Carbide Chemical and Plastics Company, Inc., Speciality Chemicals Division, (Reprinted from Handbook of Water–Soluble Gums and Resins), pp. 19–1–19–33.

*Rolyax Water–soluble Resins*, Association Compounds, Union Carbide Chemicals Division, p. 22, 1991.

*Seprafilm™ Bioresorbable Membrane, Product Monograph for the Reduction of Postsurgical Adhesions*, Genzyme Corporation, 1–29, 1996.

Kitano, et al., *Viscous Carboxymethylcellulose in the Prevention of Epidural Scar Formation*, Spine, vol. 16, No. 7, Jul. 1991.

*Hercules Cellulose Gum, Sodium Carboxymethylcellulose, Chemical and Physical Properties*, Hercules, Inc., 1–31, 1984.

Takayma, et al., *Effect of Interpolymer Complex Formation on Bioadhesive Property and Drug Release Phenomenon of Compressed Tablet Consisting of Chitosan and Sodium Hyaluronate*, Chem. Pharm. Bull., 38(7), 1993–1997, 1990.

Aurora, et al., *Pathology of Peritoneal Adhesions—An Experimental Study*, Indian J. Med. Res., 62, 4, 539–544, Apr. 1974.

Harlanc, et al., *Polyelectrolyte Gels, Properties, Preparation, and Applications*, American Chemical Society Symposium Series, Nov. 11–16, 1990, 480.

Feddersen, et al., *Sodium Carboxymethylcellulose*, Industrial Gums, Polysaccharides and Their Derivatives, Third Edition, 537–579, 1993.

Steizer, et al., *Carboxymethylcellulose*, Handbook of Water––Soluble Gums and ResinsChapter 4, pp. 4–1–4–28, 1980.

Danishefsky, et al., *Conversion of Carboxyl Groups of Mucopolysaccharides into Amides of Amino Acid Esters*, Carbohyd. Res., 16, 199–205, 1971.

Tsuchida, et al., *Interactions Between Macromolecules in Solution and Intermacromolecular Complexes*, Advance Polymer Science, 45–122, 1982.

Anseth, et al., *Mechanical properties of hydrogels and their experimental determination*, Biomaterials, 17, 1647–1657, 1996.

Kofinas, et al., *Development of methods for quantitative characterization of network morphology in pharmaceutical hydrogels*, Biomaterials, Vo. 18, No. 20, 1361–1369.

Agrawal, et al., *Technique to Control pH in Vicinity of Biodegrading PLA–PGA Implants, John Wiley & Sons, Inc.,* 1997, pp. 105–114.

Hunt, et al., "Silica Aerogel, A Transparent High Performance Insulator," *Proceedings of the International Solar Energy Society World Congress*, Sep. 13–18, 1987, Hamburg, West Germany, pp. 1–5.

Tewari, et al., "Microstructural Studies of Transparent Silica Gels and Aerogels," *Proceedings of the 1986 Spring Meeting of the Materials Research Society*, Apr. 15–19, 1986, Palo Alto, CA., pp. 1–11.

Hunt, et al., "Process Considerations in Monolithic Aerogels," *Materials Research Society*, 1988, Materials Research Society Symposium, vol. 121, pp. 679–684.

Lenacrt, Ph.D., et al., "Bioadhesive Drug Delivery Systems," *CRC Press, Inc.*, 1990, pp. 25–168.

Loffus, et al., "Colloidal and Kinetic Principles of Sol–Gel Processing," *Advanced Materials '90*, Mar. 1990.

POLYACID/POLYALKYLENE OXIDE FOAMS AND GELS AND METHODS FOR THEIR DELIVERY

RELATED CASES

This application claims priority under 35 U.S.C. § 120 to U.S. Provisional Patent Application Ser. No. 60/200,637, filed Apr. 28, 2000, and United States Utility patent application Ser. No.: 09/472,110, filed Dec. 27, 1999, both applications herein incorporated fully by reference. This application is also related to United States Utility Patent Application titled "Hemostatic Compositions of Polyacids and Polyalkylene Oxides and Methods for Their Use", Stephanie M. Cortese, Herbert E. Schwartz, and William G. Oppelt, inventors, application Ser. No. 09/843588 filed concurrently, incorporated herein fully by reference.

FIELD OF THE INVENTION

This invention relates generally to the delivery and use of polyacid/polyether complexes, cross-linked gels comprising polyacids, polyalkylene oxides and multivalent ions, the formation and delivery of foams and gels to inhibit the formation of adhesions between tissues and to promote hemostasis.

BACKGROUND OF THE INVENTION

Adhesions are unwanted tissue growths occurring between layers of adjacent bodily tissue or between tissues and internal organs. Adhesions commonly form during the healing which follows surgical procedures, and when present, adhesions can prevent the normal motions of those tissues and organs with respect to their neighboring structures.

The medical and scientific communities have studied ways of reducing the formation of post-surgical adhesions by the use of high molecular weight carboxyl-containing biopolymers. These biopolymers can form hydrated gels which act as physical barriers to separate tissues from each other during healing, so that adhesions between normally adjacent structures do not form. After healing is substantially complete, the barrier is no longer needed, and should be eliminated from the body to permit more normal function of the affected tissues.

Schwartz et al (U.S. Pat. Nos. 5,906,997, 6,017,301, and 6,034,140) describe membranes, hydrogels and association complexes of carboxypolysaccharides and polyethers for use as antiadhesion compositions. Because of the presence of polyethers in membranes made using these materials, these compositions exhibited certain antithrombogenic properties, including decreased platelet adhesion, decreased platelet activation, and decreased binding of fibrin and blood clots to membranes. U.S. patent application Ser. No.: 09/472,110, incorporated herein fully by reference, disclosed that multivalent cations including $Fe^{3+}$, $Al^{3+}$, and $Ca^{2+}$, and/or polycations including polylysine and polyarginine can be used to provide intermolecular attraction, thereby providing a means of controlling viscoelastic properties of gels.

Davies et al. (U.S. Pat. No. : 5,169,037 and RE35,540) describe pressurized canisters having a product bag therein.

Stoffel (U.S. Pat. No. 5,126,086) describes a pressurized container having an inner bag for delivery of product.

Obrist (U.S. Pat. No. 5,799,469) describes a method of manufacture and a pressure pack having an outer container and a bag for holding the product to be dispensed.

Patterson (U.S. Pat. No. 4,350, 272) describes a barrier package having a controlled release coating that can peel from the package and form a barrier between the product and propellant.

Prior art delivery systems are depicted in FIGS. 1 and 2. FIG. 1 depicts a delivery system having a canister 100, comprising a top 103 and a bottom 118, having a bag 102 therein, to contain the product to be delivered. The bag is sealed with gusset 105, and has valve mechanism 117 with an actuator 101. The top 106 of bag 102 is shown suspended from the valve mechanism 117.

FIG. 2 depicts a prior art delivery system similar to that shown in FIG. 1, but additionally having a delivery tube 120.

There is need for improved antiadhesion products, including foams, that can be used quickly and efficiently by surgeons so as to achieve desired clinical results.

SUMMARY OF THE INVENTION

In certain aspects, this invention comprises new antiadhesion foams and methods and devices for delivering antiadhesion gels, sprays or foams. The antiadhesion product to be delivered is placed in a canister under pressure, and when a valve is opened, the product exits the canister and can be delivered to a surgical site. In embodiments in which the antiadhesion composition is in direct contact with a propellant gas, when delivered, the composition can be in the form of a foam. In embodiments in which the antiadhesion composition is separated from the propellant gas, the composition can be delivered as a gel or a spray.

In other embodiments, a gas capsule is mounted within the canister to increase the amount of antiadhesion product delivered. A gas capsule is an additional pressure storage chamber within a first pressure storage chamber that is used for propellant. As the pressure in the first storage chamber becomes depleted as the propellant is discharged, the gas capsule can provide additional propellant to expel more of the product from the canister. A gas capsule can be used in any situation, not limited to delivery of antiadhesion compositions, in which it is desirable to deliver more of the contents of the canister than can be delivered using a simple single-compartment pressure system. In certain of these embodiments, the gas capsule can be charged prior to insertion within the canister. In other embodiments, the gas capsule can be charged while inside the canister. Upon charging, the gas capsule can be pressurized to the same degree as the canister. In certain embodiments, the gas capsule can be adapted to open only when the pressure within the gas capsule compared to the canister pressure exceeds a desired threshold. Thus, when a portion of the antiadhesion product has been delivered and the pressure within the canister is reduced, the higher pressure within the secondary source can open a valve and transiently increase the pressure in the canister to permit additional product to be expelled from the canister.

The types of antiadhesion compositions is not limited by the delivery system. Any antiadhesion composition can be delivered if the physical properties of the composition are compatible with pressure delivery. In one aspect of the invention, a composition can be desirable that comprises a foam of an intermacromolecular association of a polyacid ("PA") such as a carboxypolysaccharide (CPS) and a polyalkylene oxide ("PO") such as a polyether (PE), for example, a polyethylene oxide ("PEO"). Antiadhesion compositions based on association complexation between ionically associated or hydrogen bonded polyacids ("PA") and hydrophilic polyalkylene oxides ("PO") can have different hemostatic, antiadhesion, and other physiological properties depending upon the pH, the PO and the PA contents, the total solids content, as well as other properties of the composition. As described further below, the PA of this invention can be made with polyacrylic acid, carboxypolysaccharides such as CMC, and other polyacids known in the art. Ionically cross-linked gels of this invention can be made by mixing polyacid and polyether together, either in dry form or in aqueous solution, and then adding a solution containing cations to provide cross-linking between the PA, the PO and the cations. The pH of the composition can be adjusted. The gels can then be sterilized and stored before use.

The compositions of this invention can be used to inhibit post-surgical adhesions, to decrease the consequences of arthritis, and/or to provide a lubricant for numerous medical and/or veterinary uses. The gels and foams of this invention can be used in conjunction with antiadhesion membranes to provide rapidly acting hemostatic effects, and longer-lasting antiadhesion properties. These properties of antiadhesion compositions can improve wound healing from traumatic injuries and/or surgeries.

Additionally, in accordance with some aspects of the invention, drugs can be included in the membranes or gels to deliver pharmacological compounds directly to the tissues. Certain of these embodiments can include the use of thrombin or other hemostatic agents to further inhibit bleeding at a surgical or wound site.

In certain embodiments, the compositions can be sterilized using thermal methods, gamma irradiation, ethylene oxide, and ion beams which can alter the physical and other properties of the components. Alternatively, in other embodiments of this invention, the materials can be filter sterilized. The materials are biocompatible, and can be cleared from the body within a desired period of time, thereby reducing chronic adverse effects.

BRIEF DESCRIPTION OF THE DRAWINGS

The invention will be described with respect to particular embodiments thereof. Other objects, features, and advantages of the invention will become apparent with reference to the specification and drawings in which:

FIG. 4a depicts a charged gas capsule with little transmural pressure across the capsule.

FIG. 4b depicts the charged gas capsule of FIG. 4a wherein a significant trans mural pressure across the capsule has flexed resilient members of the gas capsule.

FIG. 4c depicts the gas capsule as in FIGS. 4a–4b wherein the transmural pressure had exceeded that needed to open the capsule and release the propellant.

FIG. 5a depicts a charged gas capsule having a piston.

FIG. 5b depicts a gas capsule as in FIG. 5a in which the piston has moved in response to decreasing transmural pressure.

FIG. 7a depicts a delivery system of this invention having a gas capsule and no product bag.

FIG. 7b depicts a delivery system of this invention having a gas capsule and a product bag.

DETAILED DESCRIPTION

Definitions

Figure 1:
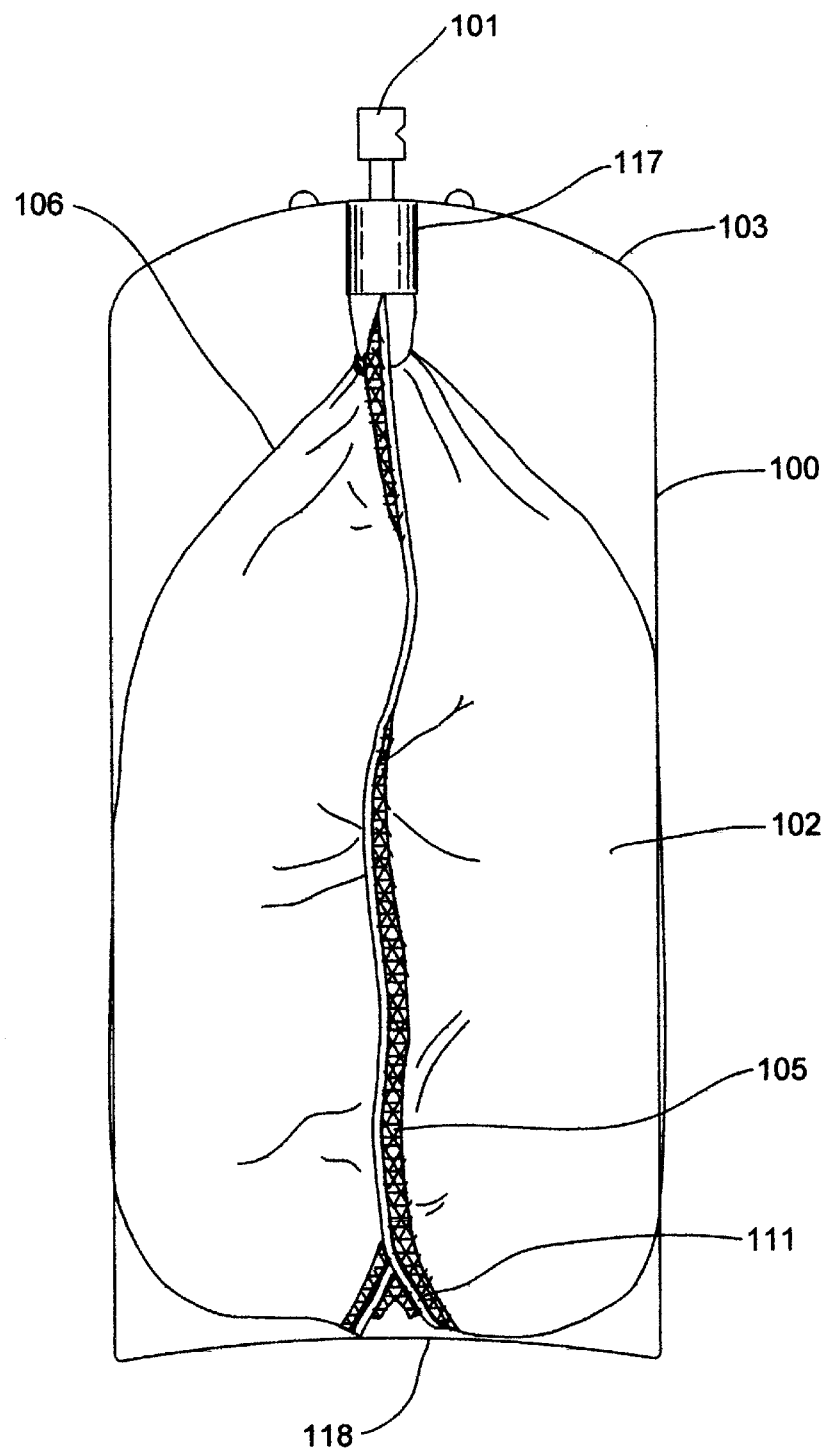
FIG. 1 depicts a pressurized delivery system of the prior art.
Figure 2:
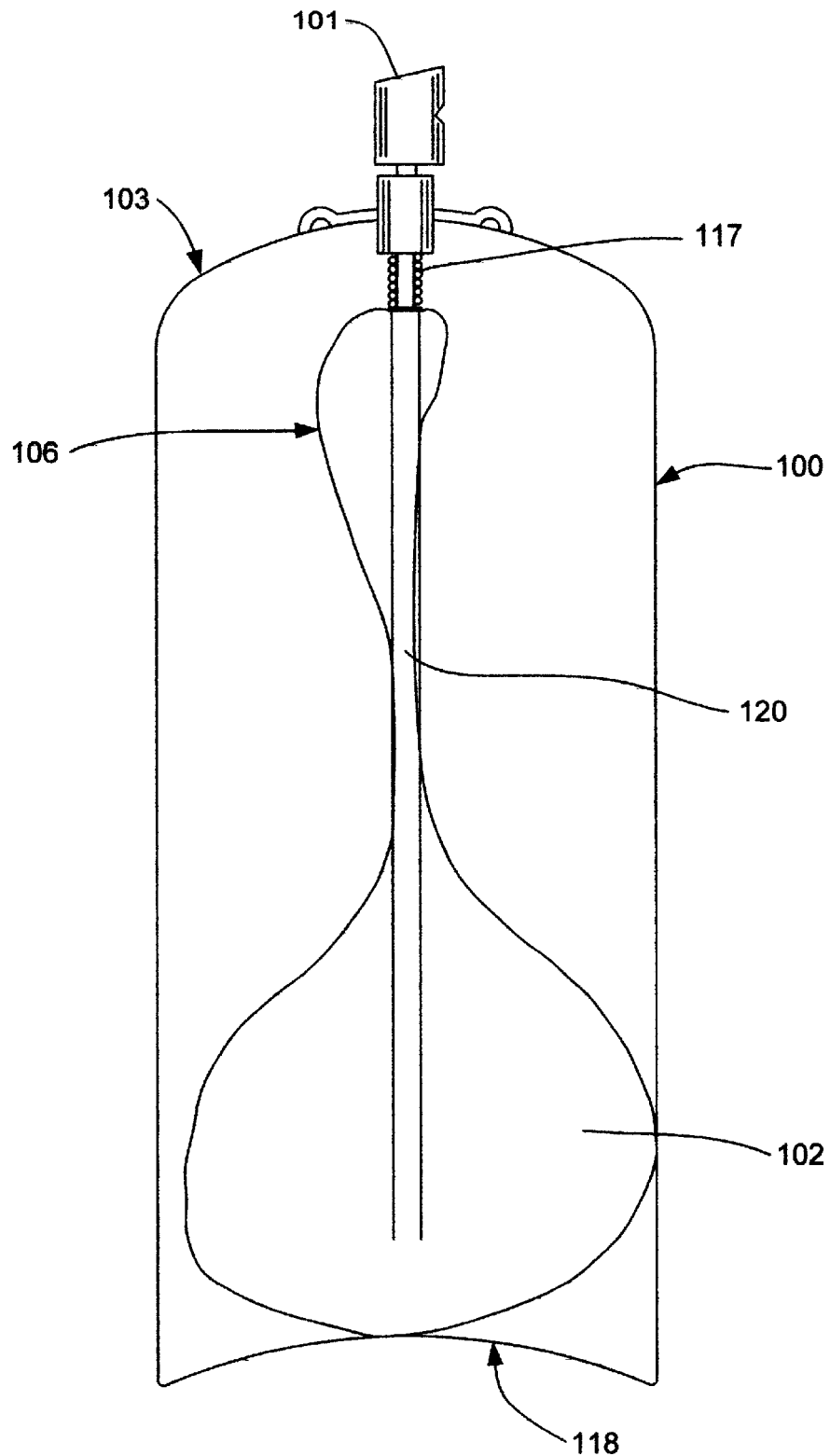
FIG. 2 depicts a pressurized delivery system of the prior art.

Before describing the invention in detail, the following terms are defined as used herein.

The term "adhesion" means abnormal attachments between tissues and organs that form after an inflammatory stimulus such as surgical trauma.

The terms "adhesion prevention" and "anti-adhesion" means preventing or inhibiting the formation of post-surgical scar and fibrous bands between traumatized tissues, and between traumatized and nontraumatized tissues.

The term "antithrombogenic" means decreased adherence of platelets, decreased platelet activation, decreased fibrin adherence, and/or decreased blood clot adherence to the anti-adhesion composition.

The term "association complex" or "intermacromolecular complex" means the molecular network formed between polymers containing CPS, polyacids, PE, polyalkylene oxide and/or multivalent ions, wherein the network is cross-linked through hydrogen and/or ionic bonds.

The term "bioadhesive" means being capable of adhering to living tissue.

The term "bioresorbable" means being capable of being reabsorbed and eliminated from the body.

The term "biocompatible" means being physiologically acceptable to a living tissue and organism.

The term "carboxymethylcellulose" ("CMC") means a polymer composed of repeating carboxylated cellobiose units, further composed of two anhydroglucose units (β-glucopyranose residues), joined by 1,4 glucosidic linkages. The cellobiose units are variably carboxylated.

The term "carboxypolysaccharide" ("CPS") means a polymer composed of repeating units of one or more monosaccharides, and wherein at least one of the monosaccharide units has a hydroxyl residue substituted with a carboxyl residue.

The term "chemical gel" means a gel network comprised of covalently cross-linked polymers.

The term "degree of substitution" ("d.s.") means the average number of carboxyl or other anionic residues present per mole of cellobiose or other polymer.

The term "discectomy" means a surgical operation whereby a ruptured vertebral disc is removed.

The term "endoscope" means a fiber optic device for close observation of tissues within the body, such as a laparoscope or arthroscope.

The term "fibrous tissue" means a scar or adhesions.

The term "foam" means a gel having bubbles of a foaming gas.

The term "gel pH" means the pH of the gel or the pH of the casting solution from which the gel or a partially dried form of the gel is formed.

The term "hemostasis" means cessation of bleeding from a surgical or trauma site.

The term "hemostatic agent" means a drug or a chemical that promotes hemostasis.

The term "hyaluronic acid" ("HA") means an anionic polysaccharide composed of repeat disaccharide units of N-acetylglucosamine and glucuronic acid. HA is a natural component of the extracellular matrix in connective tissue.

The term "hydration" (also "swelling") means the process of taking up solvent by a polymer solution.

The term "hydrogel" means a three-dimensional network of hydrophilic polymers in which a large amount of water is present.

The term "laminectomy" means a surgical procedure wherein one or more vertebral lamina are removed.

The term "mesothelium" means the epithelium lining the pleural, pericardial and peritoneal cavities.

The term "peritoneum" means the serous membrane lining the abdominal cavity and surrounding the viscera.

The terms "physical gel," "physical network" and "pseudo gel" mean non-covalently cross-linked polymer networks wherein the association of polymers in these gels is characterized by relatively weak and potentially reversible chain-chain interactions, which can be comprised of hydrogen bonding, ionic association, ionic bonding, hydrophobic interaction, cross-linking by crystalline segments, and/or solvent complexation.

The term "polyacid" ("PA") means a molecule comprising subunits having dissociable acidic groups.

The term "polyalkylene oxide" ("PO") means non-ionic polymers comprising alkylene oxide monomers. Examples of polyalkylene oxides include polyethylene oxide (PEO), polypropylene oxide (PPO) and polyethylene glycol (PEG), or block copolymers comprising PO and/or PPO.

The term "polycation" means a polymer containing multiple positively charged moieties. Examples of polycations include polylysine, polyarginine, and chitosan.

The term "polyethylene glycol" ("PEG") means a non-ionic polyether polymer being composed of ethylene oxide monomers, and having a molecular weight in the range of about 200 daltons ("d") to about 5000 daltons.

The term "polyethylene oxide" ("PEO") means the non-ionic polyether polymer composed of ethylene oxide monomers The molecular weight of PEO as used herein is between 5,000 d and 8,000 kilodaltons ("d").

The term "solids" used with reference to polymer compositions means the total polymer content as a weight percentage of the total weight of the composition.

The term "solids ratio" means the percentage of the total dry polymer contents as a weight percentage of the total solids content.

The term "tissue ischemia" means deprivation of blood flow to living tissues.

The term "transmural pressure" means the static pressure on one side of a structure or wall minus the static pressure on the other side of the structure or wall. For example, for a gas capsule, the transmural pressure is the pressure inside the capsule minus the pressure outside the capsule.

DETAILED DESCRIPTION OF THE INVENTION

Certain embodiments of the present invention are directed to compositions and methods of delivering antiadhesion products. Antiadhesion products, in general, can reduce the formation of adhesions during and following surgery and/or wound healing. This is carried out by delivering to a wound or a tissue involved in a surgical procedure, an implantable, bioresorbable association complex of a polyacid (PA), a polyalkylene oxide (PO), a polyether (PE), a polyethylene glycol (PEG), and/or multivalent ions and/or polycations. Complexes in gel or foam form can generally be made by mixing appropriate amounts and compositions of CPS and PE together in solution, then if desired, by adjusting the pH, and finally, by loading the product into a pressurized canister.

The antiadhesion products delivered by the systems of this invention can have additional physiological properties, including bioresorbability, antithrombogenicity and hemostatic properties. Discussion of these properties of antiadhesion compositions is provided in U.S. patent application Ser. No: 09/472,110, incorporated herein fully by reference and in the concurrently filed United States Utility Patent Application titled "Hemostatic Compositions of Polyacids and Polyalkylene Oxides and Methods for Their Use," Stephanie M. Cortese, Herbert E. Schwartz, and William G. Oppelt, inventors. The above Patent Applications are incorporated herein fully by reference.

To form foams, the hydrogel or association complex can be charged with a gas, such as a propellant gas, at increased pressure. Upon releasing the pressure, the dissolved gas expands to create the foam. The foam is applied to the surgical site, and adheres to the tissues which, during wound healing, would otherwise tend to form adhesions between them. Some of the gas escapes from the foam and the foam returns to a more gel-like state. The complex remains at the site for different periods of time, depending upon its composition, method of manufacture, and upon the form of delivery.

To deliver gels and sprays using the devices and methods of this invention, the antiadhesion composition is separated from the propellant gas, for example, by using a bag. The canister is then pressurized, but because the bag is not highly permeable to the gas, the gas does not substantially dissolve in the composition. When the pressure is released upon delivery of the gel to the tissue, the composition does not expand and a foam does not form. Similarly, if the viscosity of the composition is sufficiently low, the composition can be delivered as a spray or mist.

When the tissues have substantially healed, the complex then degrades and/or dissolves and is cleared from the body.

A possible mechanism for formation of cross-linked gels and foams of this invention is discussed in U.S. Pat. No. 5,906,997, incorporated herein fully by reference. This possible mechanism involves the formation of hydrogen bonds between PA and PO moieties in solution. Further, adding multivalent cations can form additional, ionic bonding between the PA, PO and cations. These possible mechanisms are for illustration only, and are not intended to be limiting. Other mechanisms may be responsible for the effects of the compositions of this invention.

I. Compositions of Hemostatic, Antiadhesion Membranes, Gels and Foams

The carboxypolysaccharide, polyether and other components of the compositions of this invention may be of any biocompatible sort, including but not limited to those described in U.S. Pat. No. 5,906,997 and U.S. patent application Ser. No.: 09/472,110.

The pH of the compositions of the present invention may be below about 7, between 1 and 7, alternatively between 2 and 7, in other embodiments, between 2.5 and 7, in other embodiments, between 3 and 7, and in yet other embodiments, between 3.5 and 6.0. For certain uses, a pH of about 4 can be desired where there is a balance between the bioadhesiveness, hemostasis, antiadhesion properties, the rates of bioresorbability and the biocompatability for several uses contemplated in the present invention. In other embodiments of this invention, the pH can be below about 6.0, in other embodiments, below about 5.0, in yet other embodiments below about 4.0 and in yet further embodiments, below about 3.0. We unexpectedly found that decreasing pH can increase hemostatic properties of PA/PO compositions.

Like other polymers which are known to swell when exposed to water, PA/PO gels and foams are also bioadhesive. A possible reason for this phenomenon is that with increased hydration, more charges on the polyacid become exposed, and therefore may be made available to bind to tissue proteins. However, excessive hydration is detrimental to bioadhesion. Thus, a means of controlling the bioadhesiveness of membranes is to control their hydration properties.

In addition to decreasing the pH of the association complex, increased intermacromolecular association can be achieved using carboxylated PAs, such as CPSs, with increased degree of carboxyl substitution. By increasing the density of protonatable carboxyl residues on the CPS, there is increasing likelihood of hydrogen bond formation even at a relatively high pH. The degree of substitution of CPS must be greater than 0, i.e., there must be some carboxyl residues available for hydrogen bond formation. However, the upper limit is theoretically 3 for cellulose derivatives, wherein for each mole of the saccharide, 3 moles of carboxyl residues may exist. Thus, in the broadest application of the invention involving CPS as the polyacid, the d.s. is greater than 0 and up to and including 3. In other embodiments, the d.s. is between 0.3 and 2. CPS with d.s. between 0.5 and 1.7 work well, and CPSs with a d.s. of about 0.65–1.45 work well and are commercially available.

The complexes of the instant invention are intended to have a finite residence time in the body. Once placed at a surgical or wound site, or site of inflammation, the foam is designed to serve as a hemostatic barrier for a limited time period. Once healing has substantially taken place, the anti-adhesion barrier can naturally dissolve and be cleared from the body. The time taken to clear the body for certain embodiments is desirable no more than 29 days because of increased regulation by the Food and Drug Administration of devices intended to remain within the body for more than 30 days. However, it can be desirable to provide longer-duration compositions for certain long-term uses.

The mechanisms for bioresorption of PA/PO complexes are not well understood. However, an early step in the process of bioresorption is solubilization of the network of polyacid and polyalkylene oxide. For example, when soluble, CMC and PEO can diffuse into the circulation and be carried to the liver and kidneys, where they may be metabolized or otherwise eliminated from the body. Additionally, enzymatic action can degrade carbohydrates. It is possible that enzymes contained in neutrophils and other inflammatory cells may degrade the polymer networks and thereby increase the rate of elimination of the components from the body.

The degradation and rate of solubilization and disruption of the membrane is manipulated by careful adjustment of the pH during formation of the association complexes, by varying the CPS/PE ratio, and by selecting the appropriate degree of substitution of the CPS and molecular weights of the PE and CPS. Decreasing the molecular weight of CPS increases its solubility. The strength of the membrane can be tailored to the surgical application. For example, certain surgical applications (e.g., spine or tendon) may require a stronger, more durable membrane than others (such as intraperitoneal applications). Manipulation of the above-mentioned variables allows the manufacture and use of products with variable residence times in the body.

Biocompatability of CPS/PE complexes of the present invention can be a function of its acidity. A highly acidic complex contributes a relatively larger total acid load to a tissue than does a more neutral complex. Additionally, the more rapidly hydrogen ions dissociate from a complex, the more rapidly physiological mechanisms must compensate for the acid load by buffering, dilution and other mechanisms. To mimic the rate and total amount of acid given up by a membrane in vivo, membranes are placed in PBS solutions and the degree of acidification of the PBS is measured. In addition to membrane pH, membrane composition also influences the acid load delivered to the body. Moreover, by using a foam preparation, in certain embodiments, the total solids content of the antiadhesion dose can be less than for either non-foam gels or for membranes. Therefore, the total load of acid delivered to a tissue by an acidic foam can be reduced, decreasing any adverse effects of the composition's acidity.

A. Polyacid/Polyalkylene Oxide Gels and Foams

Other embodiments of the present invention are directed to ionically and non-ionically cross-linked gels and foams for reducing surgical adhesions, providing hemostasis, decreasing the symptoms of arthritis, and providing biologically compatible lubricants. Embodiments can incorporate hemostatic agents including thrombin, vasoconstrictors, fibrillar collagen, and the like. Vasoconstrictors include adrenergic agonists such as norepinephrine, epinephrine, phenylpropanolamine, dopamine, metaraminol, methoxamine, ephedrine, and propylhexedrine. Methods for accomplishing these aims comprise the step of delivering to a wound or other biological site, an implantable, bioresorbable composition comprised of a polyacid and a polyether which are associated with each other by way of hydrogen bonding, ionic bonding, ionic association or ionic cross-linking.

Certain embodiments having relatively little intermolecular bonding can be more readily resorbed than embodiments having more bonding. Thus, increasing intermolecular bonding can increase residence time of the composition in the body, and therefore can remain at the site for a longer period of time than compositions having smaller degrees of intermolecular bonding. By way of example, by selecting compositions which provide the highest viscosity (see below), the residence time can be adjusted to provide a desired lifetime of antiadhesion effect. Additionally, in certain other embodiments, the compositions can be dried to form a membrane, which can further increase the residence time at a tissue site. Thus, by selecting the chemical composition of the gel, and by selecting the form of the composition (e.g., gel or foam), a desired combination of properties can be achieved to suit particular needs.

B. Gel Structures

The gels of this invention are termed "physical gels." The term physical gels has been used (de Gennes, P. G. *Scaling*

Concepts in Polymer Physics. Ithaca, N.Y. Cornell University Press, p, 133, (1979)) to describe non-covalently cross-linked polymer networks. Physical gels are distinguished from "chemical gels" which are covalently cross-linked. Physical gels are relatively weak and have potentially reversible chain-chain interactions which may be comprised of hydrogen bonds, ionic association, hydrophobic interaction, stereo-complex formation, cross-linking by crystalline segments, and/or solvent complexation.

Ionically cross-linked gels can be made by mixing appropriate amounts and compositions of polyacids, polyether and cross-linking cations together in a solution. Non-ionically cross-linked association complexes can be made by altering the pH of the PA/PO mixture. In general, reducing the pH can increase the number of potential hydrogen bonding sites between the polymer molecules. Additionally, and optionally, the solution can be acidified to promote cross-linking of the polyacid and polyether molecules through hydrogen bonds as described for carboxypolysaccharides and polyethers above and in U.S. Pat. Nos. 5,906,997; 6,017,301; 6,034,140; U.S. patent application Ser. No.: 09/252,147, filed Feb. 18, 1999, and U.S. patent application Ser. No.: 09/472,110, filed Dec. 27, 1999. Each aforementioned Patent and Application is herein incorporated fully by reference. The antiadhesion gels useful for this invention can have viscosities up to about 2,000,000 centipoise ('cps"). In other embodiments, the viscosity can be in the range of about 500 cps to about 1,500,000 cps, and alternatively about 1000 cps to about 500,000 cps. In general, the viscosity can be selected to provide a balance between desired bioadhesiveness, antiadhesion efficacy and ease of delivery using the systems of this invention.

Membranes can be made by pouring a solution of PA and PO, with or without multivalent cations onto a suitable flat surface, such as a tray, and permitting the mixture to dry to form a membrane at either reduced (>0.01 Torr) or normal (about 760 Torr) atmospheric pressure. The compositions can be placed near tissues which, during wound healing, would form adhesions. The complex can remain at the site for different periods of time, depending upon its composition, method of manufacture and the form of delivery. When the tissues have substantially healed, the complex can then dissolve and be cleared from the body.

Gels and membranes in accordance with the invention can be made with desired degrees of viscosity, rigidity, different rates of bioresorbability, different degrees of bioadhesion, different degrees of anti-adhesion effectiveness and different degrees of hemostatic and antithrombogenic properties.

Compositions of PA and PO require only that the solutions of PA and PO can be handled easily during manufacture, and can be easily dispensed through the nozzle of the delivery system. In general, with increased total solids content, the viscosity of the composition tends to increase, and if the viscosity of the material is too high, then delivery rates typically can be decreased. Thus, the viscosity chosen for delivery using the methods and apparatus of this invention can depend on the pressure, nozzle diameter and desired delivery rates. Dilute solutions (up to about 10% weight/volume) of CPS are easy to handle, and solutions of about 2% CPS are easier to handle. Solutions of PEO up to about 20% (weight/volume) are possible to make and handle, and solutions of about 1% by weight are easy to handle. However, the maximal concentration can be increased if the molecular weight of the PE is reduced. By way of example only, PEG having a molecular weight of about 1000 Daltons can be made in a concentration of about 50%. Further decreasing the molecular weight of the PE can permit even higher concentrations to be made and handled easily.

C. Polyacid Components

The polyacid may be of any biocompatible sort. By way of example, a group of polyacids useful for the present hemostatic invention are carboxypolysaccharides (CPS) including carboxymethyl cellulose (CMC), carboxyethyl cellulose, chitin, carboxymethyl chitin, hyaluronic acid, alginate, pectin, carboxymethyl dextran, carboxymethyl chitosan, and glycosaminoglycans such as heparin, heparin sulfate, and chondroitin sulfate. Additionally, polyuronic acids such as polymannuronic acid, polyglucuronic acid, and polyguluronic acid, as well as propylene glycol alginate can be used. In addition to the CPS, polyacrylic acids, polyamino acids, polylactic acid, polyglycolic acids, polymethacrylic acid, polyterephthalic acid, polyhydroxybutyric acid, polyphosphoric acid, polystyrenesulfonic acid, and other biocompatible polyacids known in the art are suitable for making gels, foams and sprays. Such polyacids are described in *Biodegradable Hydrogels for Drug Delivery*, Park et al., Ed., Technomic Publishing Company, Basel, Switzerland (1993), incorporated herein fully by reference. Preferably, carboxymethylcellulose or carboxyethylcellulose is used. More preferably, carboxymethylcellulose (CMC) is used. The molecular weight of the carboxypolysaccharide can vary from 10 kd to 10,000 kd. CPS in the range of from 600 kd to 1000 kd work well, and CPS of 700 kd works well, and is easily obtained commercially.

D. Polyalkylene Oxide Components

Similarly, many polyalkylene oxides can be used. These include polypropylene oxide (PPO), PEG, and PEO and block co-polymers of PEO and PPO, such as Pluronics™ (a trademark of BASF Corporation, North Mount Olive, N.J.). The preferred PO of the present invention is polyethylene oxide (PEO) having molecular weights of between about 5,000 Daltons (d) and about 8,000 Kd. Additionally, polyethylene glycols (PEG) having molecular weights between about 200 d and about 5 kd are useful.

The inclusion of a polyether in the complex confers antithrombogenic properties which help prevent adhesions by decreasing the adherence of blood proteins and platelets to a composition (M. Amiji, *Biomaterials*, 16:593–599 (1995); Merill, E. W., *PEO and Blood Contact in Polyethylene Glycol Chemistry-Biotechnical and Biomedical Applications*, Harris J. M. (ed), Plenum Press, New York, 1992; Chaikof et al., *A. I. Ch. E. Journal* 36(7):994–1002 (1990)). PEO-containing compositions impair the access of fibrin clots to tissue surfaces, even more so than a composition containing CMC alone. The inclusion of PE to the gels also can increase the spreading or coating ability of the gel onto biological tissues. By increasing the spreading, there is increased likelihood that the gel can more efficiently coat more of the tissue and thereby can decrease the likelihood of formation of adhesions at sites remote from the injured tissue.

Varying the ratios and concentrations of the polyacid, the polyether and multivalent cations or polycations can alter hemostatic and antithrombogenic properties. In general, increasing the amount of CPS and decreasing the amount of PO can increase hemostasis, whereas increasing the amount of PO an decreasing the amount of CPS can decrease hemostasis.

The percentage ratio of polyacid to PO may be from about 10% to 99% by weight, alternatively between about 50% and about 99%, and in another embodiment about 90% to about 99%. Conversely, when the PO is PE, the percentage of PE can be from about 1% to about 90%, alternatively from about 1% to about 50%, and in another embodiment, about 1% to 10%. In another embodiment, the amount of PE can be about 2.5%.

E. Ionic Components

The tightness of the association and thus the physical properties of the association complex between the PA and PO may be closely regulated by selection of appropriate multivalent cations. In certain embodiments, it can be desirable to use cations selected from different groups of the periodic table. Increasing the concentration and/or valence of polyvalent cations can increase ionic bonding. Therefore, trivalent ions such as $Fe^{3+}$, $Al^{3+}$, $Cr^{3+}$ can provide stronger ionic cross-linked association complexes than divalent ions such as $Ca^{2-}$, $Mg^{2+}$. $Mn^{2+}$, or $Zn^{2+}$. However, other cations can be used to cross-link the polymers of the gels of this invention. Polycations such as polylysine, polyarginine, chitosan, or any other biocompatible, polymer containing net positive charges under aqueous conditions can be used.

The anions accompanying the cations can be of any biocompatible ion. Typically, chloride (Cl) can be used, but also $PO_4^{2-}$, $HPO_3^-$, $CO_3^{2-}$, $HCO_3^-$, $SO_4^{2-}$, borates such as $B_4O_7^{2-}$ and many common anions can be used. Additionally, certain organic polyanions can be used. By way of example, citrate, oxalate and acetate can be used. In certain embodiments, it can be desirable to use hydrated ion complexes, because certain hydrated ion salts can be more easily dissolved that anhydrous salts.

Moreover, decreasing the pH of the association complex increases the amount of hydrogen cross-linking. Similarly, increasing the degree of substitution of the carboxypolysaccharide in the gel can increase cross-linking within the association complex at any given pH or ion concentration. The pH of the gels can be between about 2 and about 7.5, alternatively between about 6 and about 7.5, and in other embodiments, about 3.5 to about 6.

Gels having high solids %, or high degrees of cross-linking, such as those made using trivalent cations in the concentration range providing maximal ionic association can dissolve more slowly than gels made with lower ion concentration and/or with ions having lower valence numbers. Such gels can be used advantageously during recovery from surgery to ligaments and tendons, tissues which characteristically heal slowly. Thus, a long-lasting composition could minimize the formation of adhesions between those tissues.

F. Incorporation of Drugs into Compositions

Ionically cross-linked gels and membranes can be made which incorporate drugs to be delivered to the surgical site. Incorporation of drugs into membranes is described in Schiraldi et al., U.S. Pat. No. 4,713,243. The incorporation may be at either the manufacturing stage or added later but prior to insertion. Drugs which may inhibit adhesion formation include antithrombogenic agents such as heparin or tissue plasminogen activator, drugs which are anti-inflammatory, such as aspirin, ibuprofen, ketoprofen, or other, non-steroidal anti-inflammatory drugs. Furthermore, hormones, cytokines, osteogenic factors, chemotactic factors, proteins and peptides that contain an arginine-glycine-aspartate ("RGD") motif, analgesics or anesthetics may be added to the compositions, either during manufacture or during conditioning. Any drug or other agent which is compatible with the compositions and methods of manufacture may be used with the present invention. Desirably, to increase hemostatic properties of gels and foams, vasoconstrictors, fibrillar collagen or clotting factors including thrombin can be added.

II. Foams and Delivery Systems

Certain embodiments of delivery systems include four main components, which permit the gels to take on altered physical states upon delivery. The components include (1) an antiadhesion product, (2) a gas, (3) a pressure system, and (4) a delivery vessel. The gas in the delivery vessel, in some embodiments, serves as a foaming agent and as a propellant, permitting the compositions to be delivered easily to a wound or to either a laparoscopic or open surgical site.

Many different types of materials and devices can be used. For surgical uses, however, it can be desirable to sterilize the composition and the device using an autoclave, gamma-irradiation, electron beam irradiation or sterile ultrafiltration. Typically, conditions for autoclave sterilization includes elevated temperatures of about 250° F. for periods of from 10 to about 35 minutes. The canister, valve, product holder (if any) and other necessary components of the delivery system should be capable of withstanding the sterilization conditions. In certain embodiments, an antiadhesion composition is loaded into a bag, the bag is then sterilized, then inserted into the canister, which is then pressurized, and then the completed delivery system is sterilized. In this situation, it is not necessary to expose the contents of the canister to the prolonged times necessary to heat bag contents while in the canister, which can act as an insulator.

Foamed antiadhesion products can have distinct advantages over non-foamed products. The foam can have a relatively high volume and low density. These properties can confer the ability to spread quickly and uniformly over tissue surfaces. Further, foams can adhere to vertically oriented surfaces, making them desirable for applications to sidewalls and top areas to be treated. After application, in some embodiments, the propellant or charging gas can dissipate from the foam, so the product can lose some foam quality and can form a more gel-like coating on the tissue surface. The qualities of the foamed gels, including density, cell (or "bubble") size, life span in the foamed state, and viscosity can be controlled to achieve a desired form. In general, if a lower density antiadhesion product is desired, the gas should be chosen to provide a large cell size, causing more gas to permeate the composition. Carbon dioxide $(CO_2)$ can cause a larger cell size than nitrogen gas $(N_2)$. If a longer foam life span is desired, a higher molecular weight PEO can be added to the composition. If a higher viscosity is desired, a higher total solids content and/or more highly associated polymers can be used.

To make antiadhesion foams, typically a mixture of antiadhesion composition is exposed to increased pressure in the presence of a charging gas, including but not limited to $CO_2$, $N_2$, a noble gas such as helium, neon, argon, or any other gas that is relatively inert physiologically and does not adversely affect the polymers, drugs or other components of the mixture.

The gel material can be loaded into a pressurized canister, such as those used for aerosol applications, such as spray cans. The pressure can be any pressure that can be contained within the canister. For typical aluminum canisters, such as the CCL Industries (163 Robert Street East, Penetang, Ontario L9M 2G2 Canada) "2Q" canister, the diameter of 66 mm×542 mm can be easy for a surgeon to use. Canisters of these dimensions have a capacity of between about 385 ml to about 740 ml (about 13 to about 25 ounces). In certain embodiments, the use of a liner bag, by way of example only, "ABS" from CCL Industries can be used.

The charging gas can be introduced at a pressure of between about 1.5 and 13 atmospheres (21 pounds per square inch gauge "psig" to about 180 psig), alternatively between about 32 psig and about 140 psig, in yet other embodiments, between about 32 psig and about 109 psig, and in further embodiments, about 70 psig to about 104 psig. However, for stronger canisters, including those made of steel, higher charging pressures can be used. For example, the "18 Bar" canister from CCL Industries has a minimum buckle pressure of 261 psig and a minimum burst pressure of 313 psig. The interior of the canister desirably is lined with a material that does not adversely affect the antiadhesion composition therein. Such liners include teflon, epoxy phenolics and polyamide imides.

After charging, a valve can seal the gas and antiadhesion composition inside, and the gas is allowed to equilibrate with the mixture. Valves can be obtained commercially, and for certain uses, polypropylene valves, such as the Precision Valve Corporation (700 Nepperhan Ave., Yonkers, N.Y. 10703) 23–42 series (part No: 23-4201) can be desirable. For certain embodiments for delivery of viscous solutions, the orifice size should be selected to provide a high enough flow rate. For example, Precision Valve Corporation V 355 can be desired. This "high flow" orifice comprises four rectangular orifices, each having cross-sectional dimensions of 0.27"×0.45". The valve can be sealed to the canister cap using a gasket. In general, a desirable gasket material is Buna N, having Shore M 76. An example of such a gasket is commercially available (Precision Valve Corporation, part 05-0310). Valve springs, made of 316 stainless steel can be desirably obtained from Precision Valve Corporation (part No: 06-6070). A valve mounting cup can be used to attach the valve to the canister. For example, Precision Valve Corporation 32-17 series conical tin-plated steel cup with cut gasket (part No: 32-1790) can be desirable for the ability to withstand pressures and temperatures of charging and sterilization.

Upon releasing the pressure, such as by opening the valve, the pressure in the canister forces some of the gas/gel mixture out of the canister, thereby relieving the pressure on the gel. Some gas dissolved in the gel comes out of solution and can form bubbles in the gel, thereby forming the foam. The foam then expands until the gas pressure within the foam reaches equilibrium with the ambient pressure. In some embodiments, the bubbles can coalesce and can ultimately disperse, leaving the mixture in a gel-like state, adhering to the tissue.

In certain other embodiments, it can be desirable to include a surface-active agent in the mixture to prolong the time that the foam remains in the foamy state. Any surfactant can be used that is biocompatible and does not adversely affect the materials in the foam. Examples of such surfactants are known in the art.

In other embodiments, antiadhesion compositions can be delivered in a foamed state from a flexible liner containment system. In such situations, a charging gas need not be the same as the propellant gas. To provide such systems, the composition can be formed by introducing an antiadhesion composition into a bag along with the foaming (or charging) gas. The bag can then be placed in a pressurization container and a propellant gas can be placed, at high pressure, in the canister surrounding the bag. If the bag is relatively impermeable to the propellant gas and to the foaming gas, the resulting product can be released as a foam having only the foaming gas contained therein. This strategy can permit the use of a variety of different foaming agents and propellants.

The bubble or "cell" size and/or the density of the antiadhesion compositions can be varied by altering the type of foaming gas and/or the foaming gas pressure. Carbon dioxide, in general, can produce larger cell sizes, whereas nitrogen can produce smaller cell sizes. Larger cell sizes typically can be associated with decreased foam density, as the ratio of cell volume to surface area increases with larger cell sizes. By using a higher foaming gas pressure, more foaming gas can dissolve in the antiadhesion composition, and when the pressure is released, the cells can expand to a greater degree than for foaming gases dissolved at lower pressures. This can result in a foam having decreased density.

For example, when carbon dioxide is used as a foaming gas, the cell sizes can be in the range of about 0.008 inches (") to about 0.2" in diameter. Cell sizes in the upper range can produce foams having a "frothy" appearance and low density. In other embodiments, the cell size can be between about 0.001" to about 1.0". Densities of such frothy foams can be in the range of about 0.001 to about 1 times the density of the un-foamed composition. For foams having smaller cell sizes, the density can be higher than for "frothy" foams, being in the range of about 0.02 to about 0.9 times the density of the un-foamed composition.

Generally, small bubbles tend to empty into larger ones, as described by Laplace's law for spheres, which is well known in the physical and chemical arts. According to Laplace's law for a sphere, where at equilibrium, the transmural pressure, $\Delta P$, equals the wall tension, $T$, and the radius of curvature of the sphere, $r$, according to the formula: $\Delta P = 2T/r$. Thus, smaller cells require less wall tension than larger cells to maintain a transmural pressure gradient which would maintain bubble size. Conversely, larger bubbles require higher wall tension to maintain pressure equilibrium. Thus, if the wall tension is determined primarily by surface properties (i.e., wall thickness is not an important determinant of wall tension), then smaller cells will generate greater transmural pressure than larger cells at the same pressure, and will tend to empty into larger cells. Thus, as a foam degrades, it can pass through a stage in which cells become progressively larger with time. Foams having a wide range of cell sizes can become un-foamy relatively more rapidly than foams having more homogeneous cell sizes. The use of surfactants can partially inhibit the breakdown of the foam into a gel, by tending to equalize the transmural pressures of cells of different sizes and thereby decreasing the tendency of smaller cells to empty into larger ones.

In yet other embodiments, it can be desirable to separate cell size from density, so that a foam having a small cell size, but a high number of cells per unit volume. Adding a surfactant to the antiadhesion composition permit the manufacture of a foam having more even cell size.

Cell size can be increased by increasing the pressure of the propellant gas in the canister. In embodiments that have no liner bag, the propellant gas dissolves in the antiadhesion composition and therefore can act as a foaming gas. However, in situations in which the cell size is desired to be small, the propellant gas pressure can also be relatively small. Unfortunately, decreasing the propellant gas pressure can decrease the delivery rate of the antiadhesion composition to undesirably low values. Therefore, in certain other embodiments, a gas-impermeable product bag can be used. In these embodiments, the antiadhesion composition can be introduced into the product bag, and a relatively small amount of foaming gas can be dissolved therein. Subsequently, the propellant gas can be introduced into the canister, but outside the product bag. This results in a situation in which a relatively small volume of foaming gas can be used, while at the same time, providing a sufficiently large amount of propellant gas to ensure desirably high rates of delivery of the antiadhesion composition.

In yet other embodiments of this invention, a gel or foam can be delivered as a spray. By incorporating a specially designed orifice at the end of a flexible delivery/dispensing tube. A relatively high propellant gas pressure can cause the gel or foam to travel through the orifice at relatively high speed, thereby releasing the composition as a spray. The shape and configuration of the nozzle can be designed to achieve a desired spray profile for a specific application.

In certain laparoscopic applications, it can be necessary to deliver the antiadhesion composition through an orifice having a diameter of about 5 mm or less. The delivery tube and systems of this invention can overcome this difficulty to permit the application of high volumes of antiadhesion compositions to desired sites simply by activating a flow control mechanism on the containment vessel. In certain embodiments, the delivery/dispensing tube is of sufficient length and is sufficiently narrow to fit a 5 mm I.D. cannula commonly used in laparoscopic surgical procedures. It can also be desirable to provide a beveled nozzle on the valve or the delivery or dispensing tube, so that the direction of flow of the antiadhesion composition from the delivery system is at an angle relative to the axis of the nozzle.

In other embodiments of this invention, gas capsules can be used to provide additional pressure to aid in the expulsion of products from the canister. Several types of gas capsules are contemplated. Sufficient pressure is desirably maintained in the gas capsule so that with the release of the pressure, an additional propellant force can be exerted on the product within the canister. In general, gas capsules can have a cylindrical or other curved shape as convenient for manufacture and installation into canisters. Also, in general, smaller gas capsules can withstand higher pressures because of LaPlace's law relating transmural pressure and radius of curvature as defined above. It can be desirable for a gas capsule to maintain a transmural pressure gradient of up to about 100 psig. Alternatively, pressures in the range of about 20 psig to about 60 psig can be useful for some applications, and in other embodiments, the transmural pressure can be about 30 psig to about 45 psig. However, in other contemplated uses, the transmural pressures can exceed about 100 psig.

In one series of embodiments, a gas capsule comprises a chamber having relatively rigid sidewalls, one rigid end wall and an opposite wall having an opening and an engagement lip. A valve flap is provided that can occlude the opening, with the flap inside the engagement lip. When the valve flap occludes the opening, a pressure-tight seal is provided. By providing increased pressure of propellant gas in the gas capsule, the propellant gas, under pressure, can remain in the capsule, so long as the pressure difference between the gas capsule chamber and the surrounding environment is sufficiently low. However, as product is expelled from the canister, the pressure surrounding the gas capsule decreases, thereby increasing the pressure difference between the interior of the gas capsule and the environment. When a threshold is reached, the gas capsule can pop open as the valve flap disengages from the lip, and the pressure within the gas capsule is released into the interior of the canister. This abrupt increase in pressure can provide a propelling force driving additional product from the canister.

In alternative embodiments, gas capsules can contain pistons with or without engagement mechanisms. In certain embodiments containing engagement mechanisms, the piston can be press-fit into a cylinder, providing an interference fit that resists a tendency of the piston to move in response to a pressure differential. The engagement mechanisms can be engaged, thereby keeping the piston in the cylinder in spite of a pressure differential. The gas capsule can be placed inside a canister and the canister can be pressurized. When the canister is pressurized, the engagement mechanism can release, permitting the piston to move, albeit with limitations due to the friction caused by the interference fit of the piston with the cylinder. As the canister pressure decreases with progressive delivery of the product, the pressure within the gas capsule can force the piston out of the cylinder, thereby partially mitigating the loss of pressure from the canister. This process can tend to maintain product flow as the volume of product in the canister decreases.

The overall shape of a gas capsule can be selected to fit at desired locations within the canister. For example, a gas capsule can be placed in the bottom of the canister and can have a circular shape when viewed from the top. This "truncated cylinder" can have a diameter approximating that of the interior of the canister. In other designs, the gas capsule can be placed along a sidewall of the canister as depicted in FIG. 7, and can be either cylindrical in cross-section or can be molded to fit within the radius of curvature of the canister. In other embodiments, the gas capsule can have a narrow cross-section and a length that can be as long as the interior dimensions of the canister can permit.

In further embodiments, multiple gas capsules can be placed in a canister. In certain of these embodiments, the different gas capsules can have different thresholds for activation. A first gas capsule may be manufactured so that the capsule releases its stored propellant at a relatively high pressure, and another can release its stored propellant at a lower pressure.

In other embodiments, a gas capsule can be provided within a product bag. When the product is substantially delivered, the gas capsule can open, releasing a gas into the product bag, which can force residual product from the delivery system, and also can provide a signal to the user that the product has been substantially delivered.

VI. EXAMPLES

In the following examples, PA/PO gel compositions are described for CMC as an exemplary carboxypolysaccharide, and PEO is the exemplary polyalkylene oxide. It is understood that association complexes of other carboxypolysaccharides, other polyacids, polyethers and other polyalkylene oxides can be made and used in similar ways. Thus, the invention is not limited to these Examples, but can be practiced in any equivalent fashion without departing from the invention.

Example 1

Antiadhesion Composition Delivery System

An antiadhesion composition comprising a gel made according to methods disclosed in U.S. patent application Ser. No.: 09/472,110, incorporated herein fully by reference, was loaded into a CCL ABS canister with liner. The composition comprised 2.2% total solids, with a ratio of CMC (7HF) to PEO (8 kd) of 97.5:2.5, and included sufficient $Ca^{++}$ to provide a 60% ionically associated complex, as described in U.S. patent application Ser. No.: 09/472,110. Portions of the composition (Gel ID No: 6) were sterilized in an autoclave at a temperature of 122° C. for 35 minutes. Samples of un-autoclaved antiadhesion composition (Gel ID No: 5) and the autoclaved composition were delivered from the canister and the viscosities was measured at a spindle speed of 0.5 revolutions per minute (RPM) and the results are presented in Table 1.

TABLE 1

Gel Viscosity from Pressurized Delivery System

| Gel ID No. | Spindle # | Viscosity (1000 cps) | Measurement Temperature (C°) |
|---|---|---|---|
| 5 Autoclaved | 3 | 126 | 24.5 |
| 5 Autoclaved | 3 | 125 | 30.0 |
| 5 Autoclaved | 4 | 122 | 30.0 |
| 5 Autoclaved | 4 | 202 | 25.0 |
| 6 Not Autoclaved | 3 | >200 | 23.5 |
| 6 Not Autoclaved | 4 | 188 | 23.5 |
| 6 Not Autoclaved | 4 | 240 | 25.0 |

These results show that autoclaving decreases viscosity by about ½ on average. However, the viscosity of these preparations is sufficient to provide antiadhesion properties.

Example 2

Delivery System Containing Gas Capsule I

One embodiment of a delivery system of this invention is depicted in FIGS. 3a–3d. A delivery system 300 comprises a canister having top 103 and bottom 118, a valve 117, an actuator 101, and a flow tube 120 inside product bag 102. Gas capsule 125 is depicted at the bottom of the canister. Surrounding bag 102 is canister space 124, which is pressurized to provide a pressure differential with respect to the outside of the canister. Gas capsule consists of an outer member 125a having lip 125b, articulated hinge 125d and valve flap 125c. The components of gas capsule 125 can be made of a resilient material, including elastomeric materials that can flex upon exposure to pressure gradients. The gas capsule 125 defines gas capsule space 130 which is shown filled with charging material (stippled) under pressure. The charging material can be either a gas at all pressures ("one-phase" materials), or can be liquid at high pressures and a gas at low pressures ("two-phase" materials). For example, nitrogen gas, helium, neon, argon, or other noble gas are one-phase materials as used herein. Alternatively, hydrocarbons, fluorinated hydrocarbons can be liquids at high pressures and gases at low pressures. Many different types of two-phase materials can be used, and the relevant vapor pressures for them can be found in the Handbook of Chemistry and Physics, CRC Press, 75$^{th}$ Edition, incorporated herein fully by reference. An advantage of two-phase materials is that the pressure within the gas capsule can be held to relatively low pressures and still deliver the same volume of gas. Liquids typically occupy much less space than gases. By selecting a charging material that is liquid at the charged gas capsule pressure and a gas at the pressures encountered as the canister is being depleted of product, the gas capsule size can be minimized while still providing a desired amount of deliverable material in the capsule. Examples of two-phase materials include butane, propane, and the fluorinated fluorobutane and fluoropropane. This above list is not intended to be limiting. Many other charging materials are known in the art, and any of them can be used if they are compatible with the product or the canister.

Figure 3A:
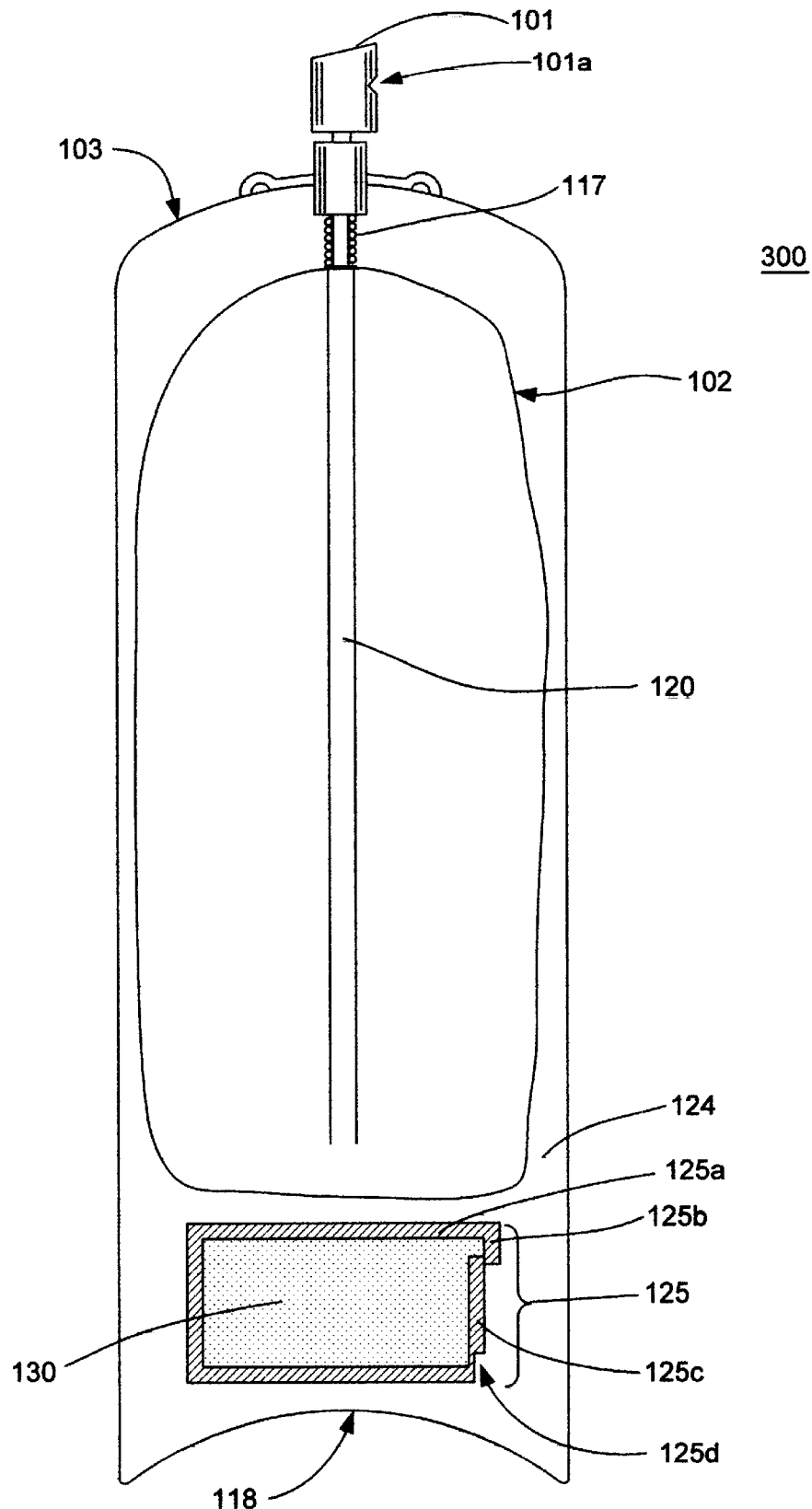
FIG. 3a depicts a delivery system of this invention comprising a gel capsule within a canister before delivery of antiadhesion composition.
Figure 3B:
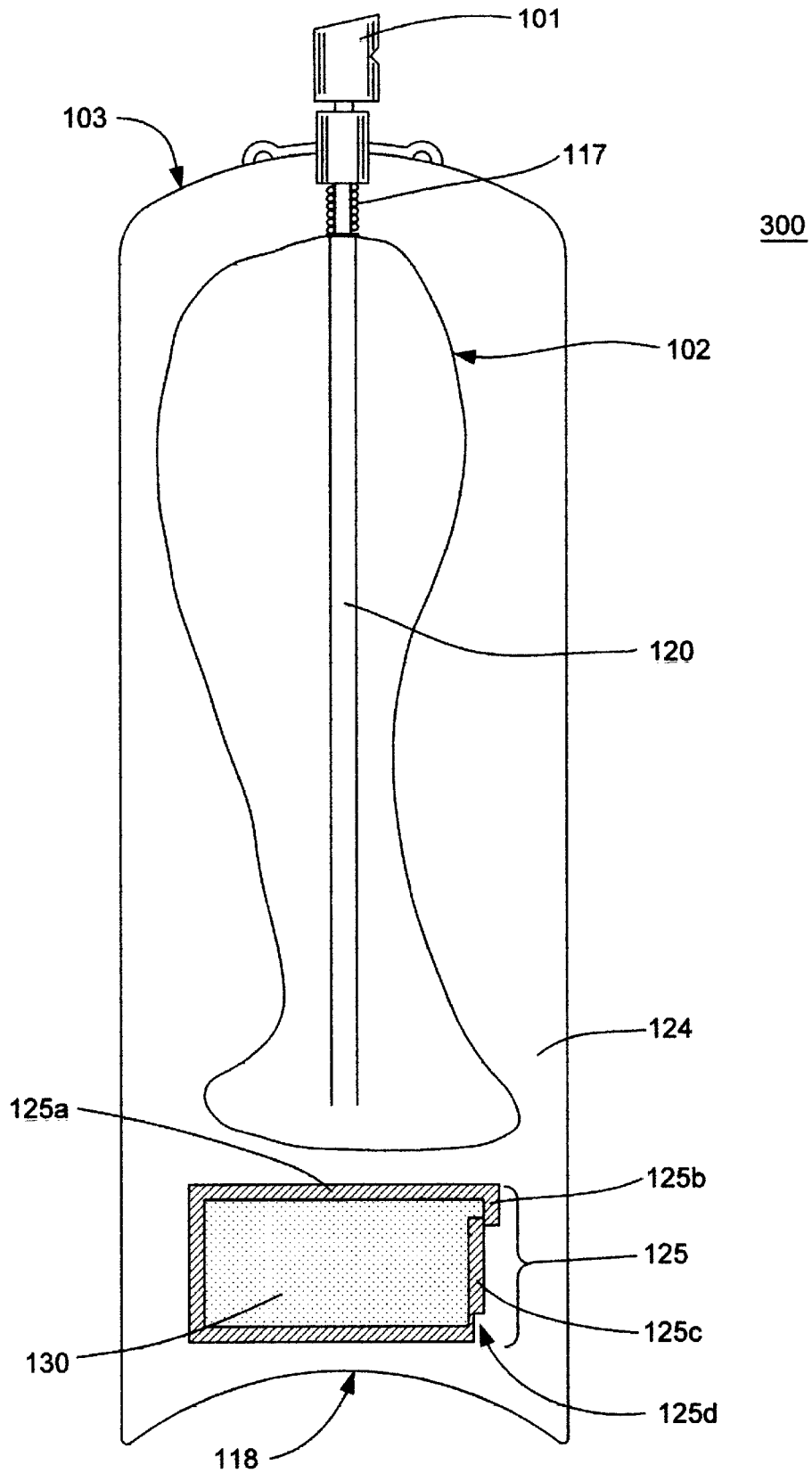
FIG. 3b depicts a delivery system as in FIG. 3b during delivery of antiadhesion composition.

FIG. 3b depicts the system as in FIG. 3a after some of the product has been delivered. Upon opening valve 117 by actuator 101, a channel is opened between bag 102 and the outside of the canister, thereby forcing product out of the nozzle 101a in actuator 101. As product is forced out of bag 102, the pressure in canister space 124 progressively decreases, thereby decreasing the pressure gradient, and therefore decreasing the flow of product out of bag 102. However, the gas capsule 125 remains sealed, and the pressure in gas capsule space remains high.

Figure 3C:
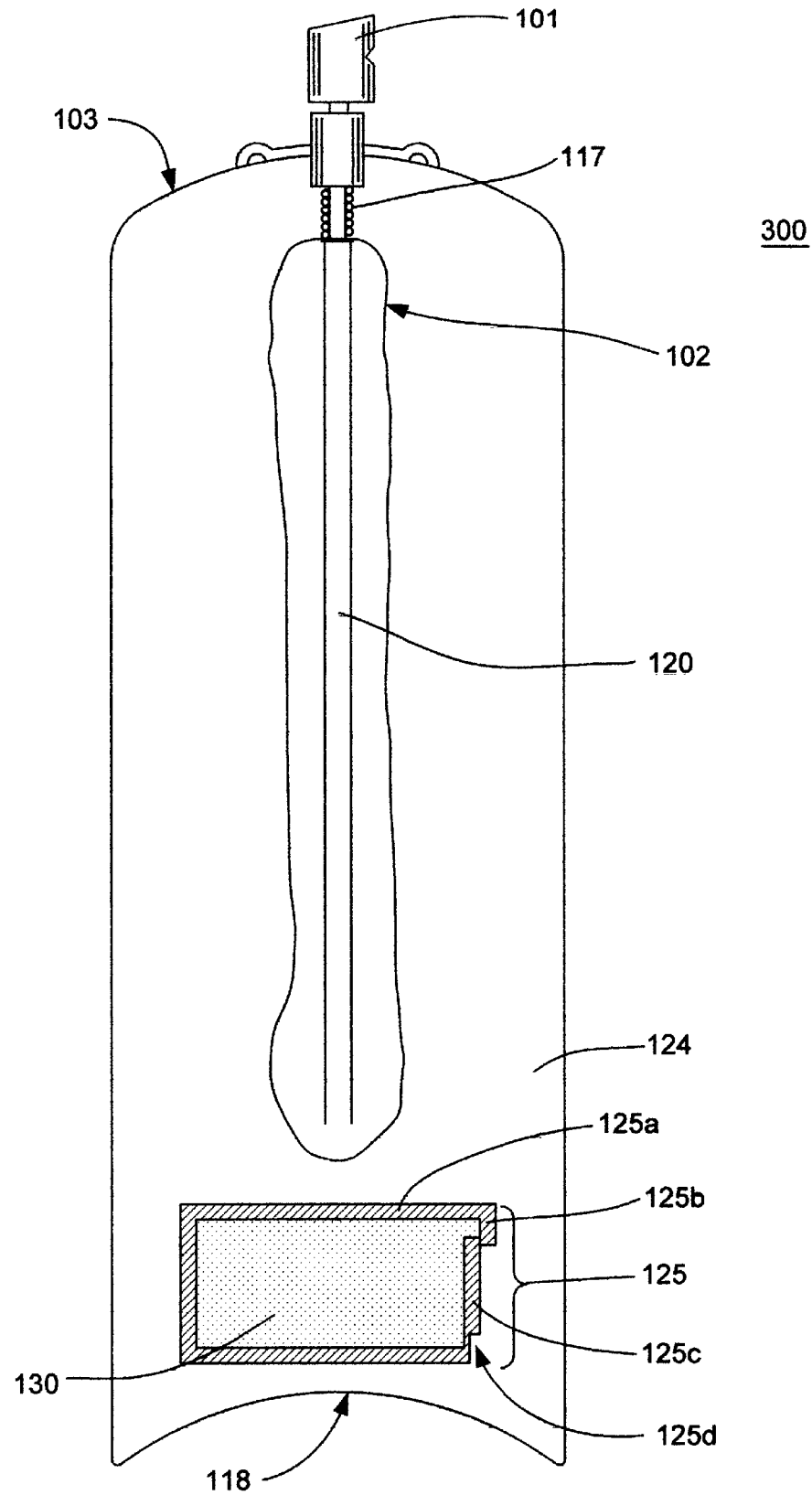
FIG. 3c depicts a delivery system as in FIGS. 3a and 3b after substantial delivery of antiadhesion composition.

In FIG. 3c, additional product has been delivered, so that bag 102 is nearly empty and the pressure in canister space 124 is further reduced compared to that in FIG. 3b. Gas capsule 125 is still sealed.

Figure 3D:
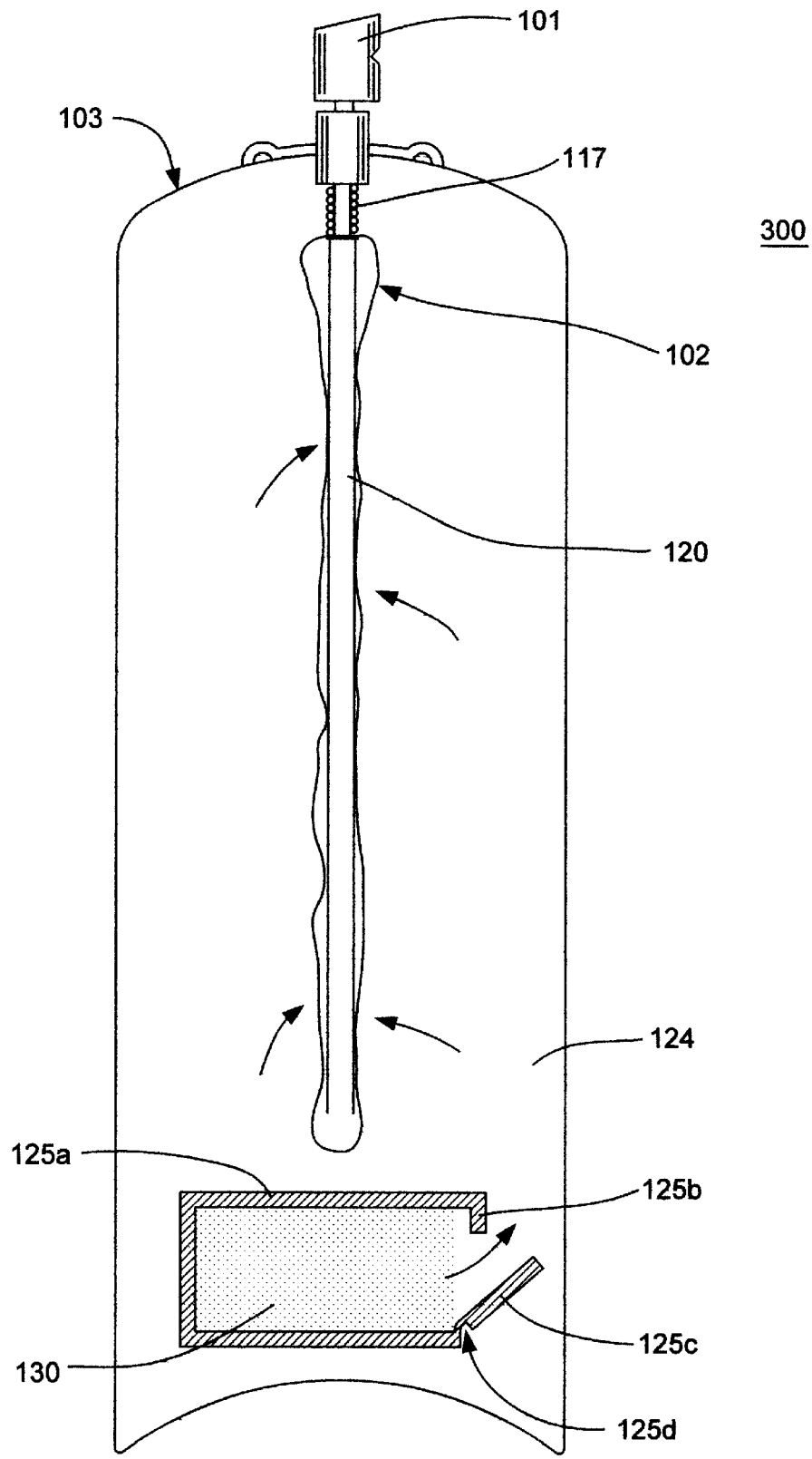
FIG. 3d depicts a delivery system as in FIG. 3a–3c after the gas capsule has opened, releasing propellant gas not the canister to expel substantially all the antiadhesion composition.

In FIG. 3d, the pressure in canister space 124 has been reduced sufficiently for the gas capsule 125 to open. The pressure gradient between gas capsule space 130 and canister space 124 has increased to the point that the resilient portions 125b, 125c, and 125d have flexed, thereby permitting valve flap 125c to be released from containment by lip 125b. Once opened, the high pressure in the gas capsule 125 causes gas within gas capsule space 130 to flow into canister space 124, thereby increasing the pressure in canister space 124. The increased pressure in canister space 124 provides driving pressure to expel additional product from bag 102 compared to the situation depicted in FIG. 3c.

Figure 4A:
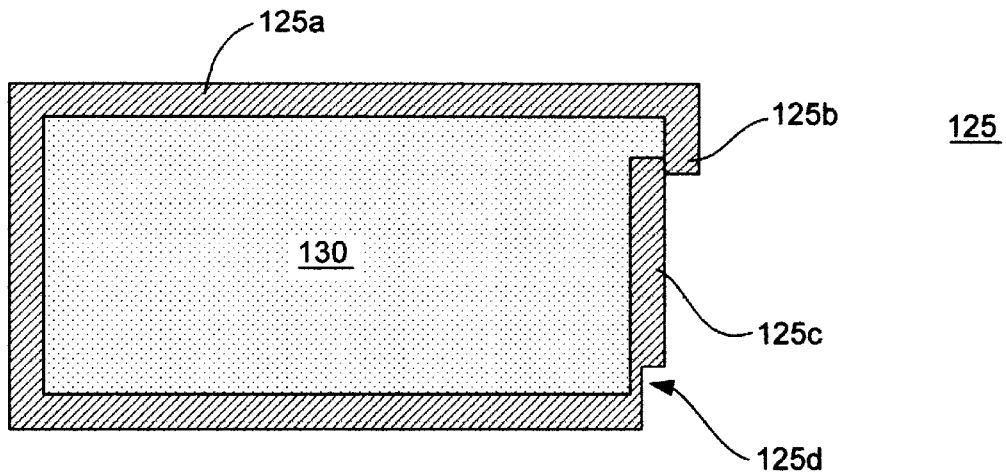
FIGS. 4a–4c depict an embodiment of a gas capsule of this invention.
Figure 4B:
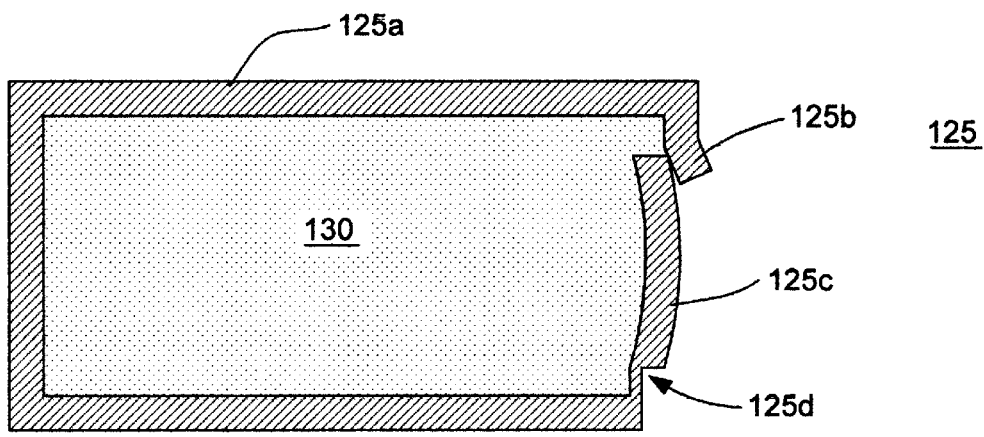
Figure 4C:
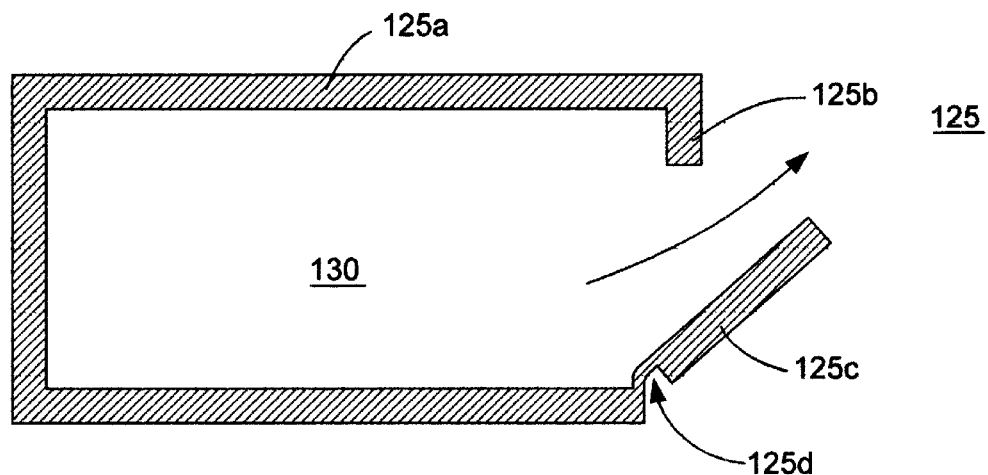

FIGS. 4a–4c depict details of the gas capsule shown in FIGS. 3a–3d. In FIG. 4a, gas capsule 125 is shown having body portion 125a, resilient lip 125b, resilient valve flap 125c and resilient hinge 125d. gas capsule space 130 is shown with pressurized gas (stippled) therein. The pressure outside the gas capsule is about as high as the pressure in gas capsule space 130, so the resilient elements are not deflected. FIG. 4b depicts a situation in which the pressure outside the gas capsule is reduced, as with progressive delivery of product from bag 102, and the accompanying drop in pressure in canister space 124 of FIG. 3c. In FIG. 4b, the pressure differential between gas capsule space 130 and the canister space is sufficiently high to deform resilient elements 125b and 125c. As elements 125b and 125c become progressively deflected, the area of overlap between lip 125b and valve flap 125c becomes progressively less. FIG. 4c depicts the situation in which the pressure differential between gas capsule space 130 and canister space 124 of FIGS. 3 is so high that the resilient elements became deflected sufficiently for the overlap between lip 125b and flap 125c to be sufficiently reduced so as to cause them to disengage from one another. The pressure in gas capsule space 130 is released, causing gas to flow out of the gas capsule space and into the canister space 124.

Example 3

Gas Capsule II

Figure 5A:
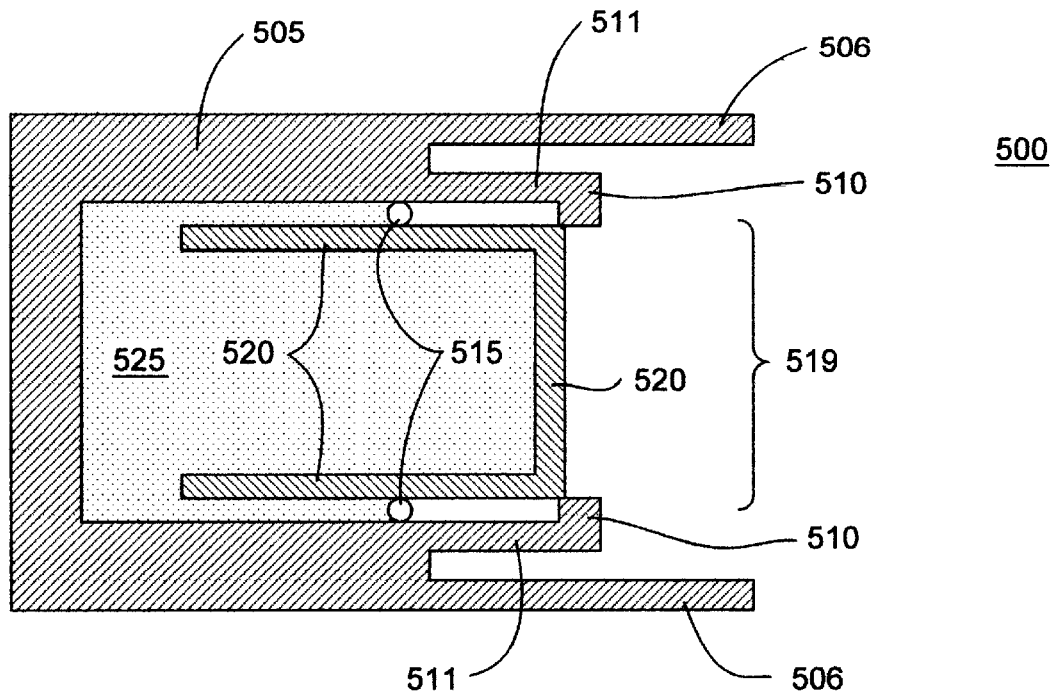
FIGS. 5a and 5b depict another embodiment of a gas capsule of this invention.

In another embodiment of this invention, a piston-type of gas capsule 500 is depicted. FIG. 5a shows capsule body 505 having support arms 506, resilient tangs 510 and points 515 that provide an interference fit with sidewalls 520 of piston 519. Tangs 510 are depicted locking the edge of piston wall 520 and thereby preventing piston 520 from being forced out of the capsule body 505. In FIG. 5a, gas capsule space 525 is filled with propellant gas (stippled). Tangs 510 are at the ends of resilient arms 511. To charge gas capsule 525, the gas capsule is maintained in a pressure chamber and the pressure is increased. Propellant gas is introduced under pressure into the capsule space 525 and piston 519 is inserted, with points 515 being spaced so as to create an interference fit with sidewalls 520 of piston 519. After capsule space 525 is pressurized, tangs 510 are flexed toward each other, thereby engaging the edges of piston 519, holding the piston 519 in place in the capsule body 505. The charged gas capsule can be then removed from the pressurizing chamber and inserted into a canister as depicted in FIG. 7. Thereafter, charging the canister to a pressure higher than the pressure in gas capsule space 525 releases the tension between tangs 510 and the edges of piston 519, thus permitting the resilient arms 511 to return to their un-flexed positions as shown. Piston 519 is held in place by points 515 interacting with sidewalls 520 of piston 519.

Figure 5B:
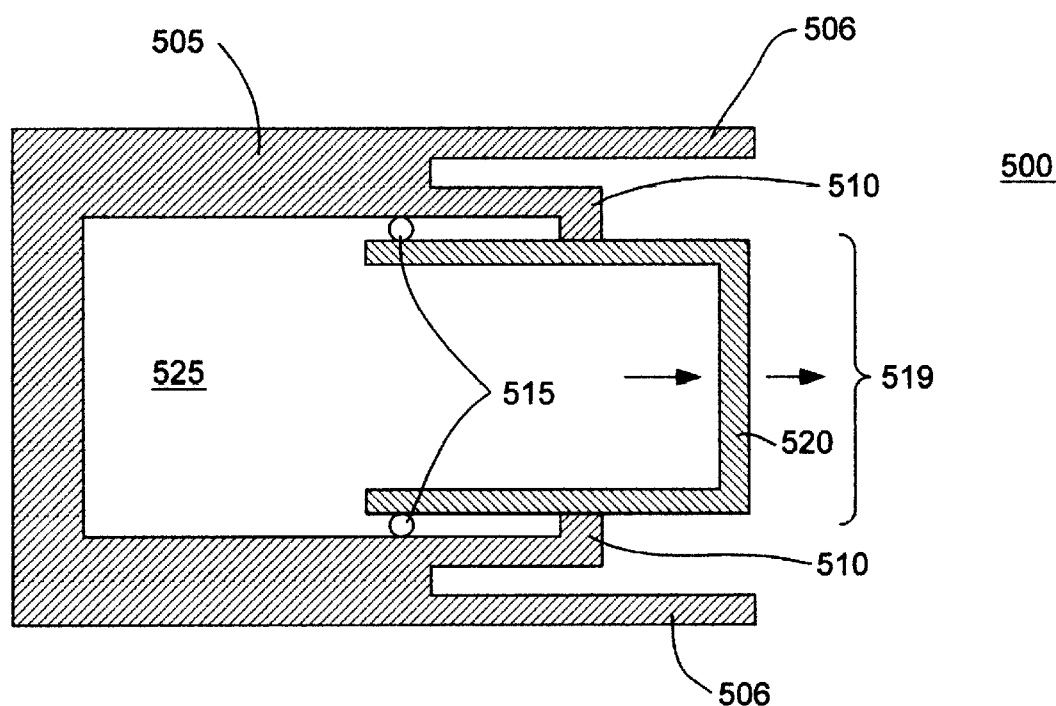

FIG. 5b depicts a gas capsule 500 of this embodiment of the invention, but after pressure in the canister space 124 of FIG. 3c has been reduced by the delivery of product from bag 102. The reduced pressure in canister space 124 provides a pressure differential between gas capsule space 525 and canister space 124, and thus provides a force on the piston walls 520 that tends to move piston 519 to the right.

Example 4

Gas Capsule III

Figure 6:
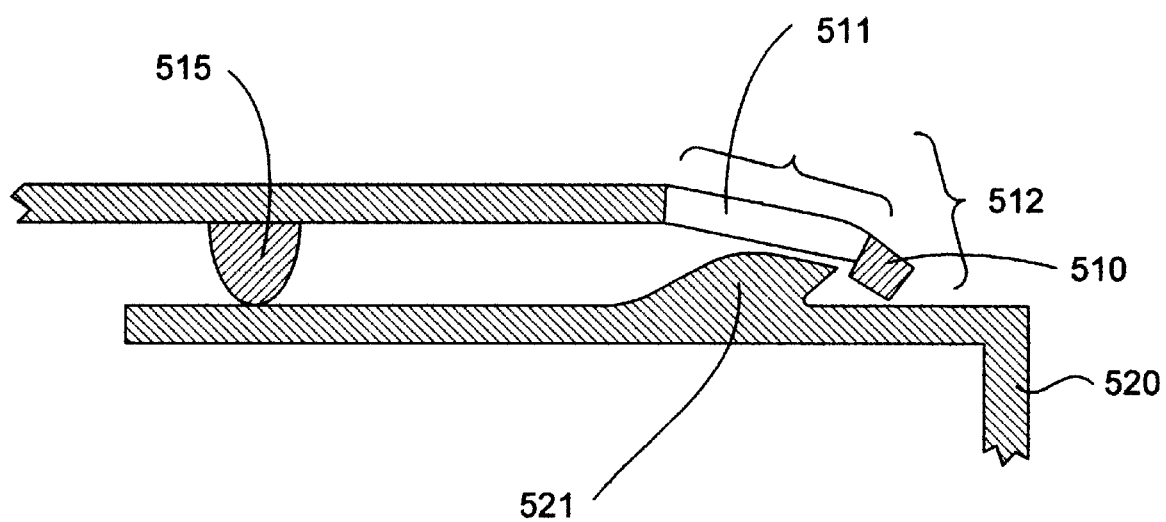
FIG. 6 depicts a detail of another embodiment of a gas capsule of this invention having a hook and a tang on a flexible arm.

FIG. 6 depicts some details of an embodiment of this invention that is similar to that depicted in FIG. 5. Piston wall 520 has hook 521 projecting upwards toward arm 512. Arm 512 is composed of a resilient portion 511 and tang 510. Arm 511 is shown flexed toward piston wall 520 and has engaged hook 521. When the gas capsule is filled with propellant gas and the compressive force on the end of the piston is released, the tendency of the propellant gas to force the piston to the right keeps tang 510 and hook 521 engaged for placement into the canister.

Example 5

Delivery System Containing Gas Capsule IV

Figure 7A:
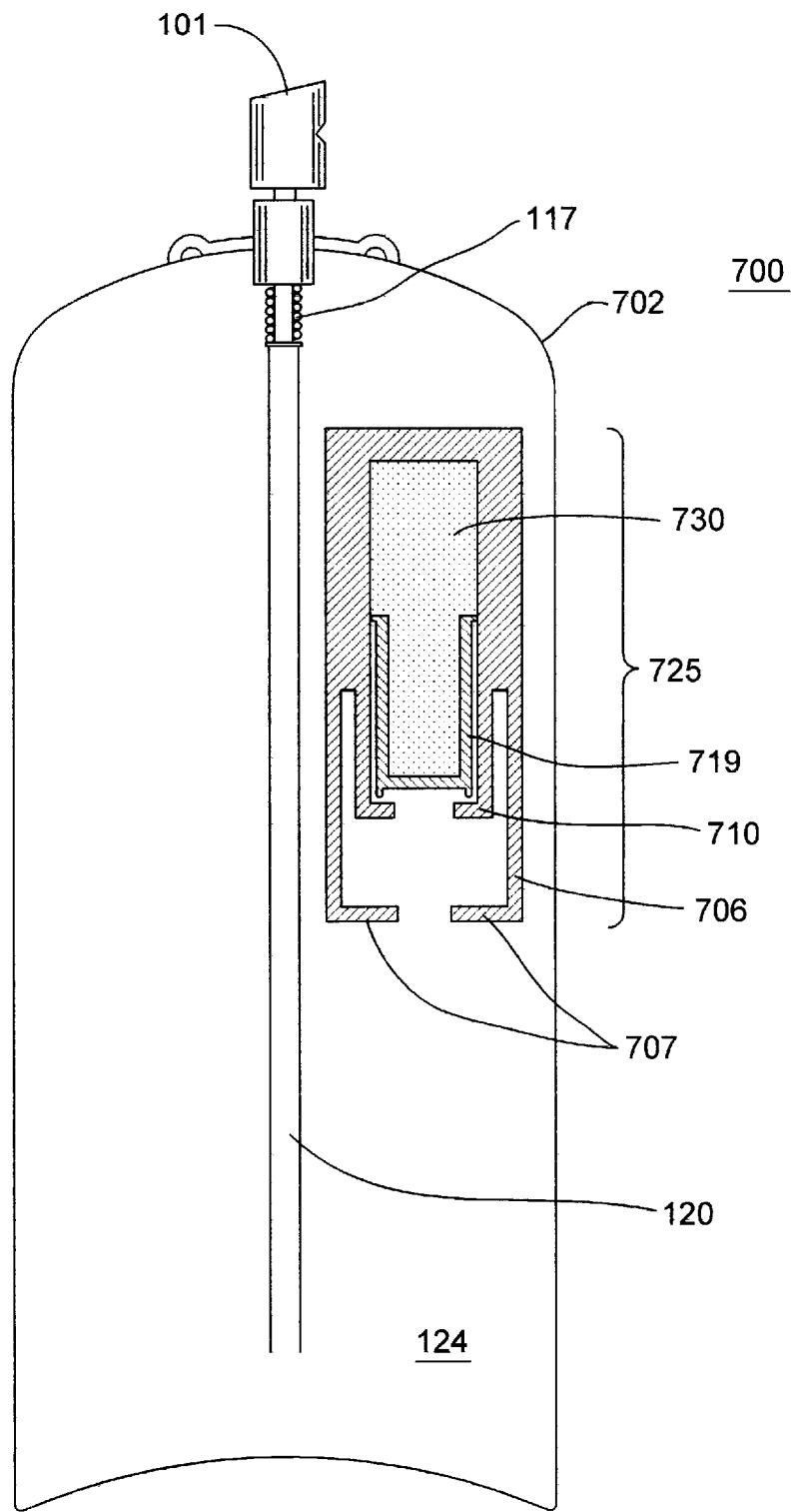
FIGS. 7a–7b depict delivery systems having a gas capsule of this invention.
Figure 7B:
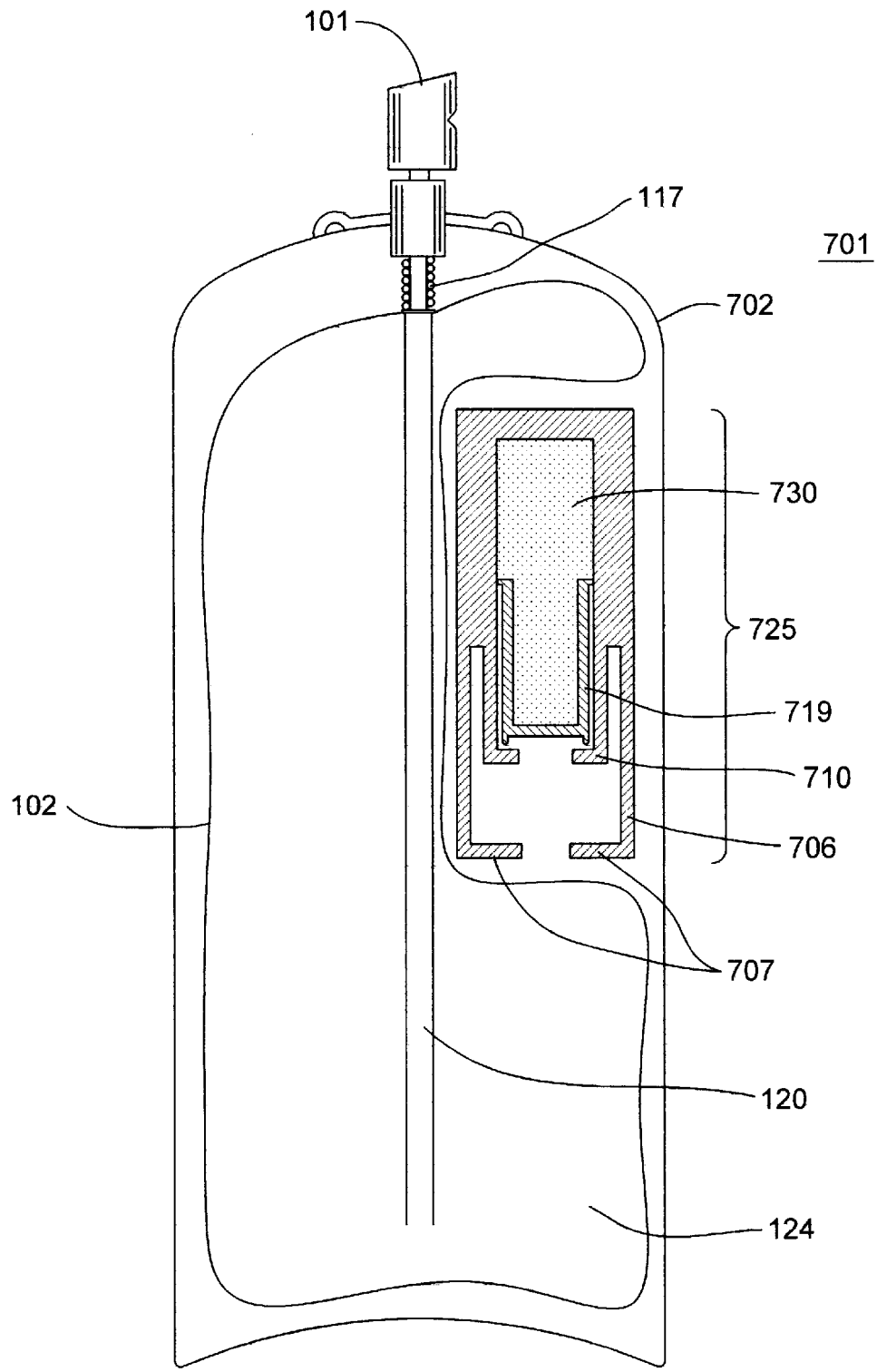

FIGS. 7a and 7b depict yet other embodiments of a gas capsule of this invention FIG. 7a depicts an embodiment 700 of this invention without a product bag. Gas capsule 725 is installed in a canister 702. Gas capsule 725 has elements as previously identified in FIGS. 5a–5b. Additionally, support arms 706 have containment lips 707 that keep piston 719 from being completely expelled from gas capsule 725. Additionally, resilient tangs 710 are depicted as engaged with the edges of piston 719, thereby hindering the free movement of piston 719 out of gas capsule 725. However, when the pressure in canister space 124 is reduced sufficiently, piston 719 moves outwardly from gas capsule 725, thereby providing an increase in pressure in canister space 124.

FIG. 7b depicts an embodiment 701 of this invention having a product bag 102. Otherwise, the elements of the gas capsule 725 are identical to those depicted in FIG. 7a.

Example 6

$CO_2$ and $N_2$ Foams

A sample of antiadhesion gel comprising a 2.2% total solids content and a ratio of CMC (7HF) to PEO (8,000 d) of 97.5:2.5 (weight percent) was made using methods described in U.S. Pat. Nos.: 5,906,997, 6,017,301, and 6,034,140, incorporated herein fully by reference. The osmolality and pH were adjusted to about 300 mOsm/kg using normal saline (0.7% NaCl) and 7.0, respectively. Samples of this antiadhesion composition were placed in each of two canisters, and one was charged with $CO_2$ at a pressure of about 100 psig, and another charged with $N_2$ gas at a pressure of about 60–70 psig.

After mixing the gases with the samples, samples of foams were delivered. Foam density was measured by filling a graduated cylinder, measuring the volume of foam delivered, and then weighing the foam. For both of the un-foamed antiadhesion compositions, the density was about 1.0 gm/ml. For the $CO_2$ foam, the density was 0.165 gm/ml, and for the $N_2$ foam, the density was 0.83 gm/ml. The cell size for the $CO_2$ foam was measured at between about 0.08" to about 0.2".

Other features, aspects and objects of the invention can be obtained from a review of the figures and the claims. All citations herein are incorporated by reference in their entirety.

It is to be understood that other embodiments of the invention can be developed and fall within the spirit and scope of the invention and claims.

We claim:

1. An antiadhesion material comprising:
   an antiadhesion composition comprising a polyacid and a polyalkylene oxide; and a foaming gas, said material being a foam.

2. The antiadhesion foam of claim 1, wherein the foaming gas is $CO_2$.

3. The antiadhesion foam of claim 1, wherein the foaming gas is $N_2$.

4. The antiadhesion foam of claim 1, wherein the polyacid is carboxymethyl cellulose and the polyalkylene oxide is polyethylene oxide.

5. The antiadhesion foam of claim 1, wherein the density of said foam is in the range of about 0.001 to about 1 times the density of the un-foamed antiadhesion composition.

6. The antiadhesion foam of claim 1, wherein said foam has a cell size of between about 0.001" to about 1.0".

7. The antiadhesion foam of claim 1, further comprising a drug.

8. The antiadhesion foam of claim 1, further comprising a hemostatic agent.

9. The antiadhesion foam of claim 1, further comprising a multivalent cation.

10. The antiadhesion foam of claim 9, wherein said multivalent cation is selected from the group consisting of calcium, aluminum, and iron.

11. The antiadhesion foam of claim 9 having a pH of below about 7.5.

12. The antiadhesion foam of claim 9 having a pH below about 6.0.

13. The antiadhesion foam of claim 9 having a pH below about 5.0.

14. The antiadhesion foam of claim 9 having a pH below about 4.0.

15. The antiadhesion foam of claim 9 having a pH below about 3.0.

16. A product comprising: an antiadhesion material comprising an antiadhesion composition comprising a polyacid and a polyalkylene oxide; and a foaming gas, said material being a foam; a canister containing said foam; a valve adapted to permit flow of said foam therethrough; and a pressure source.

* * * * *